United States Patent [19]

Heeres et al.

[11] Patent Number: 4,791,111
[45] Date of Patent: Dec. 13, 1988

[54] [[4-[4-(4-PHENYL-1-PIPERAZINYL)-PHENOXYMETHYL]-1,3-DIOXOLAN-2-YL]METHYL]-1H-IMIDAZOLES AND 1H-1,2,4-TRIAZOLES HAVING ANTI-MICROBIAL PROPERTIES

[75] Inventors: Jan Heeres, Vosselaar; Leo J. J. Backx, Arendonk; Jozef B. A. Thijssen, Kasterlee; Alfonsus G. Knaeps, Herentals, all of Belgium

[73] Assignee: Janssen Pharmaceutica, N.V., Beerse, Belgium

[21] Appl. No.: 919,400

[22] Filed: Oct. 16, 1986

Related U.S. Application Data

[63] Continuation-in-part of Ser. No. 812,670, Dec. 23, 1985, abandoned.

[51] Int. Cl.$^4$ .................. A61K 31/495; C07D 407/14; C07D 405/14
[52] U.S. Cl. ..................................... 514/252; 544/366; 544/367; 544/369; 544/370
[58] Field of Search ............... 544/366, 367, 369, 370; 514/252

[56] References Cited

U.S. PATENT DOCUMENTS

| | | | |
|---|---|---|---|
| 4,144,346 | 3/1979 | Heeres et al. | 514/252 |
| 4,267,179 | 5/1981 | Heeres et al. | 514/252 |
| 4,368,200 | 1/1983 | Heeres et al. | 514/252 |
| 4,503,055 | 3/1985 | Heeres et al. | 514/252 |
| 4,619,931 | 10/1986 | Heeres et al. | 514/252 |

FOREIGN PATENT DOCUMENTS

| | | | |
|---|---|---|---|
| 6722 | 1/1980 | European Pat. Off. | 514/252 |
| 6711 | 1/1980 | European Pat. Off. | 514/252 |
| 7696 | 2/1980 | European Pat. Off. | 514/252 |
| 118138 | 9/1984 | European Pat. Off. | 514/252 |

Primary Examiner—Donald G. Daus
Assistant Examiner—C. Shen
Attorney, Agent, or Firm—Geoffrey G. Dellenbaugh

[57] ABSTRACT

Novel [[4-[4-(4-phenyl-1-piperazinyl)phenoxymethyl]-1,3-dioxolan-2-yl]methyl]-1H-imidazoles and 1H-1,2,4-triazoles, having anti-microbial activity, compositions containing the same, and methods of inhibiting and/or eliminating the development of fungi and bacteria in warm-blooded animals suffering from diseases caused by these fungi and/or bacteria.

25 Claims, No Drawings

[[4-[4-(4-PHENYL-1-PIPERAZINYL)PHENOXYMETHYL]-1,3-DIOXOLAN-2-YL]METHYL]-1H-IMIDAZOLES AND 1H-1,2,4-TRIAZOLES HAVING ANTI-MICROBIAL PROPERTIES

CROSS-REFERENCE TO RELATED APPLICATIONS

This is a continuation-in-part of our copending application Ser. No. 812,670, filed Dec. 23, 1985, now abandoned.

BACKGROUND OF THE INVENTION

In the European Patent Publication No. 0,118,138 there are described a number of [[4-[4-(4-phenyl-1-piperazinyl)phenoxymethyl]-1.3-dioxolan-2yl]methyl]-1H-imidazoles and 1H-1,2,4-triazoles and in U.S. Pat. No. 4,267,179 there are described a number of heterocyclic derivatives of (4-phenyl-1-piperazinyl-aryloxymethyl-1,3-dioxolan-2-yl)methyl1H-imidazoles and 1H-1,2,4-triazoles, which compounds are taught to possess anti-fungal and anti-bacterial properties.

The compounds of the present invention differ therefrom by the fact that they invariably contain a 4-phenyl-1-piperazinyl moiety in which the phenyl part is substituted with a five-membered heterocycle being substituted in a previously undisclosed manner, by their favourable anti-microbial properties and particularly by their increased solubility.

DESCRIPTION OF THE PREFERRED EMBODIMENTS

This invention is concerned with 1H-imidazoles and 1H-1,2,4-triazoles having the formula

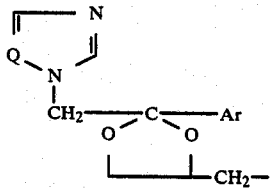

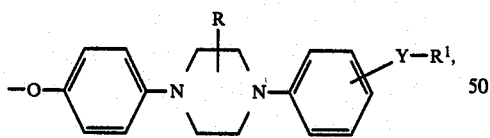

the pharmaceutically acceptable acid-addition salts and the stereochemically isomeric forms thereof, wherein
Q is N or CH;
Ar is aryl;
R is hydrogen or $C_{1-6}$ alkyl; and
Y—$R^1$ is a radical having the formula

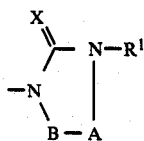

or a radical having the formula

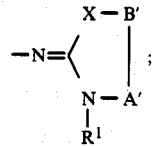

wherein
$R^1$ is tetrahydrofuranyl$C_{1-6}$ alkyl; or $C_{1-6}$ alkyl, $C_{3-6}$ cycloalkyl, aryl$C_{1-6}$ alkyl or ($C_{3-6}$ cycloalkyl)$C_{1-6}$ alkyl all substituted on the $C_{1-6}$ alkyl and/or $C_{3-6}$ cycloalkyl moiety with oxo, thioxo or with one or two radicals of formula —Z—$R^{1-a}$;
said Z being O or S;
said $R^{1-a}$ being hydrogen, $C_{1-6}$ alkyl, aryl, $C_{3-6}$ cycloalkyl or tetrahydro 2H-pyran-2-yl;
or where $R^1$ is substituted with two —Z-$R^{1-a}$ radicals, the two —$R^{1-a}$ radicals, taken together, may form a bivalent radical of formula —$CH_2$—, —$CH(CH_3)$—, —$C(CH_3)_2$—, —$CH_2$—$CH_2$—, —$CH(CH_3)$—$CH_2$— or —$CH_2$—$CH_2$—$CH_2$—;
X is O, S or $NR^2$;
said $R^2$ being hydrogen or $C_{1-6}$ alkyl;
A is >C=O, $NR^3$ or methylene, optionally substituted with up to two radicals selected from the group consisting of $C_{1-6}$ alkyl and aryl;
said $R^3$ being hydrogen or $C_{1-6}$ alkyl;
B is >C=O or methylene optionally substituted with up to two radicals selected from the group consisting of $C_{1-6}$ alkyl and $C_{1-6}$ alkyloxy;
or A and B, taken together, form a bivalent radical of formula

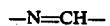 (c);

A' and B' independently having the same meaning of A and B respectively, or A' and B', taken together, form a bivalent radical of formula

 (c) or

 (d);

wherein the nitrogen atom in the bivalent radical (c) is connected to $NR^1$; wherein one hydrogen in said radical (c) and up to two hydrogens in radical (d) may be replaced by a $C_{1-6}$ alkyl radical; provided that
 (i) when Y—$R^1$ is a radical of formula (a) wherein —A—B— is other than a bivalent radical of formula (c), then $R^1$ is other than $C_{1-6}$ alkyl substituted with $C_{1-6}$ alkyloxy;
 (ii) when Y—$R^1$ is a radical of formula (b) then $R^1$ is other than $C_{1-6}$ alkyl substituted with $C_{1-6}$ alkyloxy.
wherein aryl is phenyl or substituted phenyl, said substituted phenyl having from 1 to 3 substituents each independently selected from the group consisting of halo, $C_{1-6}$ alkyl, $C_{1-6}$ alkyloxy, nitro, amino and trifluoromethyl, provided that trinitrophenyl is excluded.

In the foregoing definitions the term "halo" is generic to fluoro, chloro, bromo and iodo; the term "$C_{1-6}$ alkyl" is meant to include straight and branched hydrocarbon radicals having from 1 to 6 carbon atoms such as for example, methyl, ethyl, 1-methylethyl, 1,1-dimethylethyl, propyl, 1-methylpropyl, 2-methylpropyl, butyl, pentyl, hexyl and the like; "$C_{3-6}$ cycloalkyl" embraces cyclopropyl, cyclobutyl, cyclopentyl and cyclohexyl.

The compounds of formula (I) may contain in their structure a tautomeric system and consequently these compounds can be present in each of their tautomeric forms.

Preferred compounds within the invention are those wherein Y—$R^1$ is a radical of formula (a) or (b), wherein X, A, B, A', B' and $R^1$ are as described hereinabove, provided that A' and B', taken together, do not form a radical of formula (c) or (d).

Particularly preferred compounds within the invention are those preferred compounds wherein Y-$R^1$ is a radical of formula (a).

More particularly preferred compounds within the invention are those particularly preferred compounds wherein X is O;

A and B are independently >C=O or methylene. optionally substituted with up to two $C_{1-6}$ alkyl radicals, or A and B, taken together, form a bivalent radical of formula (c) wherein the hydrogen atom may be replaced by a $C_{1-6}$ alkyl radical; and $R^1$ is tetrahydrofuranyl $C_{1-6}$ alkyl, or $C_{3-6}$ cycloalkyl substituted with oxo or hydroxy, or $C_{1-6}$ alkyl or aryl $C_{1-6}$ alkyl both substituted on the $C_{1-6}$ alkyl moiety with oxo or with one or two radicals of formula —O—$R^{1-a}$, or where $R^1$ is substituted with two —O—$R^{1-a}$ radicals, the two —$R^{1-a}$ radicals, taken together, may form a bivalent radical of formula —$C(CH_3)_2$— or —$CH_2$—.

Especially preferred compounds within the invention are those more particularly preferred compounds wherein $R^1$ is $C_{3-6}$ cycloalkyl substituted with oxo or hydroxy, or $C_{1-6}$ alkyl or aryl $C_{1-6}$ alkyl both substituted on the $C_{1-6}$ alkyl moiety with oxo or with one or two hydroxy or $C_{1-6}$ alkyloxy radicals.

Most preferred compounds within the invention are those especially preferred compounds wherein Ar is phenyl substituted with two halo atoms: R is hydrogen: A is $C(CH_3)_2$ or $CH_2$, B is $CH_2$ or >C=O, or A and B, taken together, form a radical (c) wherein the hydrogen atom may be replaced by a methyl radical; and $R^1$ is C 6 alkyl substituted with oxo or hydroxy.

In order to simplify the structural representations of the compounds (1) and of certain starting materials and intermediates used in the preparation thereof, the 2-Ar-2-(1H-imidazol-1-ylmethyl or 1H-1,2,4-triazol-1-ylmethyl)-1,3-dioxolan-4-yl group, wherein Ar is as previously defined, will hereafter be represented by the symbol D:

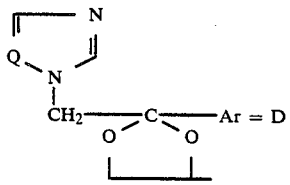

The compounds of formula (I) can be prepared by N-alkylating an intermediate of formula (II) with an appropriate reactive ester of formula (III).

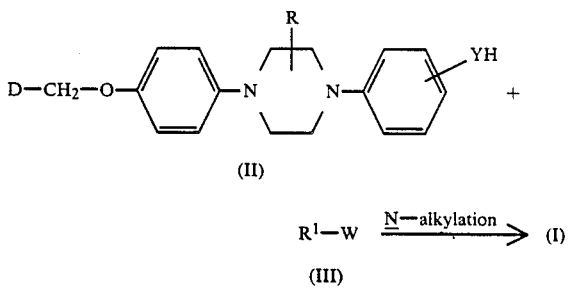

$$R^1-W \xrightarrow{\text{N—alkylation}} (I)$$

(III)

In formula (III), $R^1$ has the previously defined meaning and W is a reactive ester residue such as, for example, halo, preferably chloro, bromo or iodo, or a sulfonyloxy group such as, for example, methylsulfonyloxy, 2-naphtalenesulfonyloxy or 4-methylphenylsulfonyloxy and the like. In the particular instance where W is connected to a >C=O radical it may also represent a O—CO—$R^1$ group. Said N-alkylation reaction is conveniently conducted in a suitable reaction-inert solvent or a mixture of such solvents. Suitable reaction-inert solvents are, for example, an aromatic hydrocarbon, e.g., benzene. methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide (DMF), N,N-dimethyl-acetamide (DMA). dimethyl sulfoxide (DMSO), nitrobenzene. 1-methyl-2-pyrrolidione, and the like. An aromatic hydrocarbon, e.g., dichloromethane, trichloromethane and the like may advantageously be employed when (III) is in the form of a reactive anhydride. The addition of an appropriate base such as, for example, an alkali or an earth alkaline metal carbonate, hydrogen carbonate, hydroxide or hydride. e g , sodium hydroxide, potassium hydroxide, potassium carbonate, sodium hydride and the like or an organic base such as, for example, N,N-dimethyl-4-pyridinamine, N,N-diethylethanamine or N-(1-methylethyl)-2-propanamine may be suited to pick up the acid which is liberated during the course of the reaction. It may be advantageously previously to convert the intermediate of formula (II) into a metal salt form thereof, preferably a sodium salt, in the usual manner, e.g., by reaction of (II) with a metal base such as sodium hydride, sodium hydroxide and the like, and use said metal salt in reaction with (III). In some instances the addition of a iodide salt, preferably an alkali iodide is appropriate. Somewhat elevated temperatures and stirring may enhance the rate of the reaction.

The compounds of formula (I) can also be prepared by O-alkylating an appropriately substituted phenol of formula (V) with a reactive ester of formula (IV).

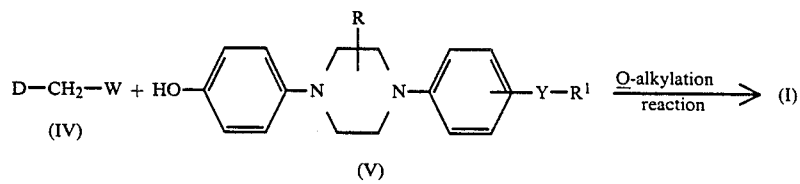

In (IV), W has the previously described meaning.

The reaction of (IV) with (V) is carried out under art-known conditions of performing O-alkylations with reactive esters. The O-alkylation reaction is conveniently conducted in a suitable reaction-inert solvent or a mixture of such solvents. Suitable reaction-inert solvents are, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone. 4-methyl-2-pentanone and the like; an ether, e.g., 1,4-dioxane, 1,1'-oxybisethane, tetrahydrofuran and the like; a polar aprotic solvent, e.g., N,N-dimethylformamide (DMF), N,N-dimethylacetamide (DMA), hexamethylphosphoric triamide (HMPT), dimethyl sulfoxide (DMSO), nitrobenzene, 1-methyl-2-pyrrolidinone; and the like. An appropriate base such as, for example, an alkali or an earth alkaline metal carbonate, hydrogen carbonate, hydroxide, alkoxide or hydride, e.g., sodium carbonate, sodium hydrogen carbonate, potassium carbonate, sodium hydroxide, sodium methoxide, sodium hydride and the like, or an organic base such as, for example, a tertiary amine, e.g., N,N-diethyl-ethanamine, N-(1-methylethyl)-2-propanamine, 4-ethylmorpholine, pyridine, quinoline, 1H-imidazole, 1H-1,2,4-triazole and the like, may be utilized to pick up the acid which is liberated during the course of the reaction. The water, the alcohol or the acid which is liberated during the course of the reaction may preferably be removed from the reaction mixture by azeotropical destillation. It may be advantageous previously to convert the substituted phenol (V) into a metal salt thereof, preferably the sodium salt, in the usual manner, e.g., by the reaction of (V) with a metal base such as sodium hydride, sodium hydroxide and the like, and to use thereafter said metal salt in the reaction with (IV). The said O-alkylation may alternatively be carried out following art-known conditions of a phase transfer reaction, in which a phase transfer catalyst catalyses the organic phase-aqueous phase reaction by extracting the ions out of the aqueous phase into the bulk organic phase where reaction can ensue. Suitable phase transfer catalysts are organic-soluble, partially water soluble catalysts, e.g., trialkylphenylmethylammonium or tetraalkylammonium halides, hydroxides and hydrogen sulfates. Somewhat elevated temperatures may be appropriate to enhance the reaction rate of the said O-alkylation and most preferably said reaction is carried out at a temperature from about 80° C. to about 130° C.

The compounds of formula (I) may also generally be prepared by first O-alkylating a substituted phenol of formula (V) with a dioxolan of formula (VI), in which W and W' independently have the meaning of W in the formula (III), provided that the leaving group capacity of W exceeds that of W', thus preparing an intermediate of formula (VII), and subsequently reacting said intermediate of formula (VII) with an azole of formula (VIII).

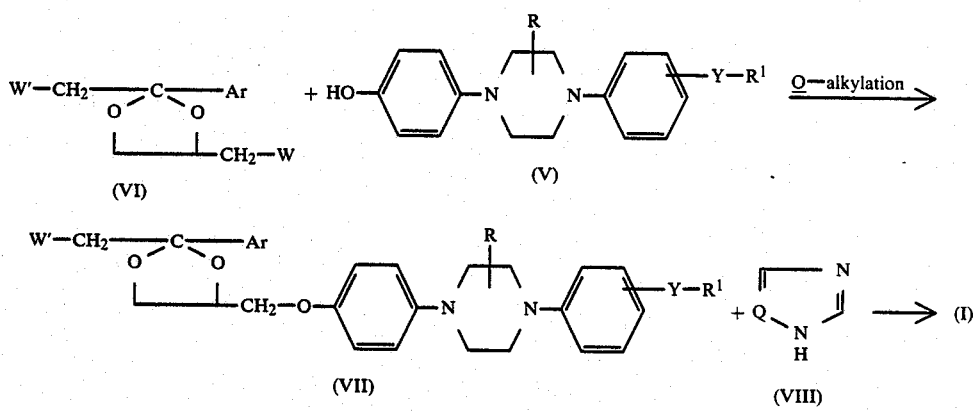

The said O-alkylation is conveniently carried out according to the procedures described hereinabove for the preparation of (I) starting from (IV) and (V).

The reaction of (VII) with (VIII) may be conducted in an appropriate organic solvent such as, for example, N,N-dimethylformamide or N,N-dimethylacetamide and the like. It may be advantageous to use an excess of azole or to add to the reaction mixture an appropriate base such as, for example, an alkali or an earth alkaline metal carbonate or hydrogen carbonate. It may particularly be advantageous previously to convert the azole, (VIII), into a metal salt from thereof by treatment with an appropriate metallating agent such as, for example, a metal alkoxide or a metal hydride. In some circumstances the addition of a iodide salt, preferably an alkali metal iodide, is appropriate. Somewhat elevated temperatures may enhance the rate of the reaction.

The compounds of formula (1) may also be prepared by reacting a ketone of formula (IX) with a 1,2-diol of formula (X), or the corresponding epoxide form thereof, in a suitable ketalizing medium.

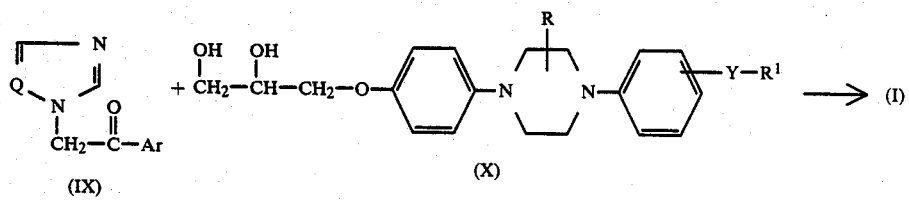

Suitable ketalizing media are mixtures containing an appropriate amount of one or more acids in a suitable solvent such as, for example, an alcohol or an aliphatic-, alicyclic- or aromatic hydrocarbon and the like. Acids which are preferably used in the said ketalizing media are relatively strong, anhydrous acids, having a pKa-value inferior to 4.

It may be advantageous to conduct the ketalization reaction at elevated temperatures and to eliminate those reaction-products which are liberated during the course of the reaction.

Additionally. the compounds of formula (I) may also be prepared by cyclizing an intermediate of formula (XI) with an amine of formula (XII) or by cyclizing an amine of formula (XIII) with an intermediate of formula (XIV).

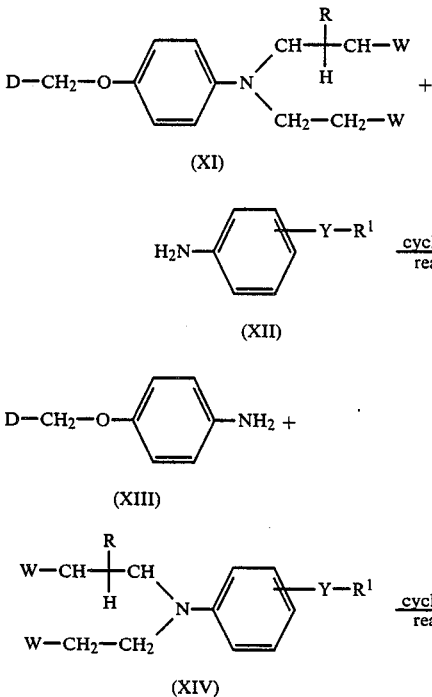

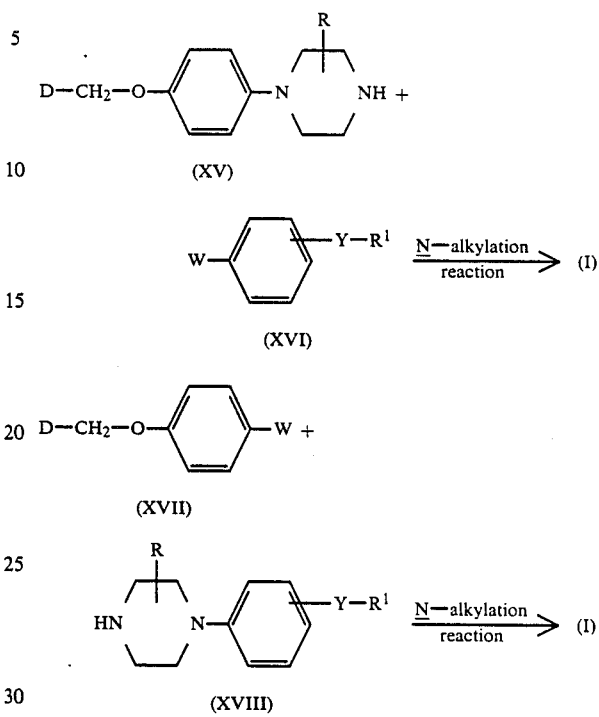

The reaction is carried out by stirring the reactants in the presence of an appropriate polar solvent. e.g., water, in admixture with an appropriate water-miscible organic solvent such as, for example, 2-propanol, 2-propanone and the like, preferably at an elevated temperature. Addition to the reaction mixture of an appropriate base, such as, for example, an alkali or an earth alkaline metal carbonate or hydrogen carbonate may be suited to pick up the acid which is liberated during the course of the reaction. In order to enhance the rate of the reaction a small amount of an appropriate iodide salt, e.g., sodium or potassium iodide may be added as a reaction promotor.

The compounds of formula (1) can also be prepared by N-alkylating a piperazine of formula (XV) with an appropriately substituted benzene of formula (XVI) or by N-alkylating a piperazine of formula (XVIII) with a benzene of formula (XVII).

Said N-alkylation reaction may be carried out in the usual manner, e.g., by stirring the reactants, preferably at somewhat elevated temperatures in an appropriate organic solvent such as, for example, dimethylsulfoxide, N,N-dimethylformamide and the like, in the presence of an appropriate base such as, for example, an alkali metal hydride or carbonate.

The compounds of formula (I) may also be prepared by cyclizing an intermediate of formula

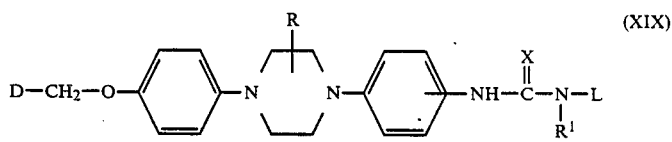

Said L in formula (XIX) being a radical —A—B—L' or —A'—B'—L' wherein L' is an appropriate leaving group.

The said cyclization reaction can generally be conducted in a suitable reaction-inert solvent such as, for example, an alcohol, e.g., butanol and the like, an ether, e.g., tetrahydrofuran, 1,4-dioxane and the like. Although the cyclization reaction may be conducted at room temperature, somewhat elevated temperatures are appropriate to enhance the rate of the reaction. Preferably the reaction is conducted at the reflux temperature of the reaction mixture. Suitable catalysts, e.g., N,N-dimethyl-4-pyridinamine, may also enhance the rate of the reaction.

The compounds of formula (I). wherein Y-R$^1$ is a radical of formula (b) wherein X is NR$^2$, said compounds being represented by the formula (I-b) may be prepared by a cyclodesulfurization reaction of an intermediate of formula (XX).

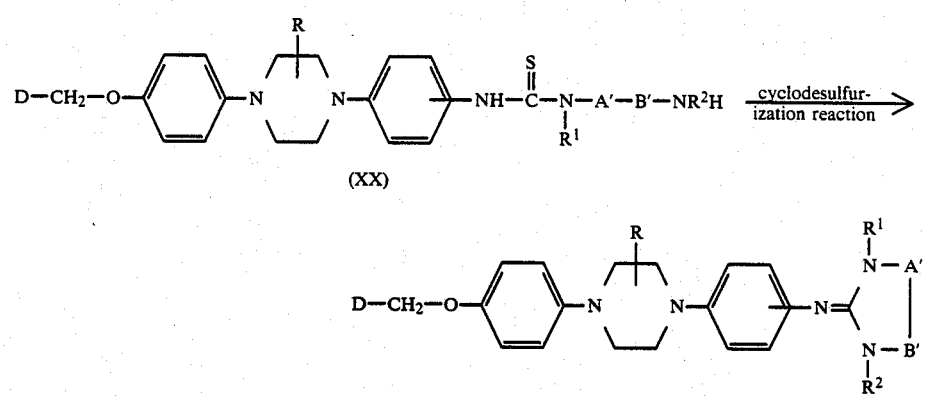

Said cyclodesulfurization reaction may be carried out by the reaction of (XX) with an appropriate alkyl halide, in an appropriate reaction-inert organic solvent, e.g., a lower alkanol. Otherwise, the cyclodesulfurization reaction may be carried out by the reaction of (XX) with an appropriate metal oxide or salt in an appropriate solvent according to art-known procedures. In certain instances it may be appropriate to supplement the reaction mixture with a small amount of sulfur. Even so methanediimines, especially N,N-methanetetraylbis[cyclohexanamine] may be used as cyclodesulfurizing agents.

The compounds of formula (I) can also be converted into each other following art-known procedures of functional group transformation. Some examples will be cited hereinafter.

Compounds of formula (1) having a hydroxy function respectively a mercapto function may be O-alkylated respectively S-alkylated with an appropriate reagent following art-known alkylation procedures.

A (tetrahydro-2H-pyran-2-yl)oxy group may conveniently be converted to a hydroxy group following art-known procedures such as, for example, by hydrolysis in acidic aqueous medium.

The compounds of formula (I) wherein $R^1$ is substituted with oxo, thioxo or with two hydroxy or mercapto radicals may be acetalized or ketalized to yield the corresponding compounds wherein $R^1$ is geminally substituted with two —Z—$R^{1-a}$ radicals, or wherein $R^1$ is substituted with a bivalent radical such as, for example, —Z—C(CH$_3$)$_2$—Z— or —Z—CH$_2$—CH$_2$—Z—. Or conversely, the latter compounds may be deketalized or deacetalized to yield the corresponding oxo, thioxo, or dihydroxy or dimercapto compounds.

Said acetalization of ketalization reaction may conveniently be conducted following art-known procedures such as, for example by reacting the starting material with an alcohol, diol, thiol or dithiol in the presence of an appropriate acid, preferably with removal of the reaction products which are formed during the course of the reaction.

Said deketalization of deacetalization may also be conducted following procedures widely known in the art such as, for example, by reacting the starting materials in an acidic aqueous medium.

Compounds of formula (1) having a >C=O function may be reduced to the corresponding alcohols following art-known carbonyl-to-alcohol reduction procedures.

The 1,uns/H/ -imidazole- and 1H-1,2,4-triazole-derivatives of formula (I). obtained in base form in the foregoing preparations, may be converted to their therapeutically active non-toxic acid addition salt forms by treatment with appropriate acids, such as, for example, inorganic acids, such as hydrohalic acid. e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The salts are in turn converted to the corresponding free bases in the usual manner, e.g., by reaction with alkali such as sodium or potassium hydroxide.

From formula (1) it is evident that the compounds of this invention have at least two asymmetric carbon atoms in their structures, namely those located in the 2- and 4-position of the dioxolane nucleus, and consequently they can exist under different stereochemically isomeric forms. The stereochemically isomeric forms of (1) and the pharmaceutically acceptable acid addition salts thereof are intended to be embraced within the scope of this invention.

The diastereomeric racemates of (I), denoted as cis and trans forms respectively, according to the rules described in J. Org Chem. 35 (9), 2849-2867 (1970), may be obtained separately by conventional methods. Appropriate methods which may advantageously be employed therefor include, for example, selective crystallization and chromatographical separation, e.g., column-chromatography.

Since the stereochemical configuration is already fixed in a number of intermediate compounds. e.g., in intermediates of the formulae (II), (IV), (VI), (VII), (XI), (XIII), (XV), (XVII), (XIX) and (XX), it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis(+), cis(−), trans(+) and trans(−) by the application of methodologies known to those skilled in the art.

A number of intermediates and starting materials used in the foregoing preparations are known compounds, others may be prepared according to art-known methodologies of preparing said or similar compounds, and others are new. A number of such preparation methods will be described hereinafter in more detail.

The intermediates of formula (II), (V), (XIX) and (XX) can conveniently be prepared following the procedures described in U.S. Pat. No. 4,267,179 and/or European patent publication No. 0,118,138.

Starting materials of formula (IV) wherein Q stands for CH and methods of preparing the same are described in Belg. Pat. No. 837,831.

In general, the reactive esters of formula (IV) can be prepared along a sequence of reactions described in U.S. Pat. No. 4,267,179 and in J. Med. Chem.,22 (8), 1003–5 (1979).

Starting materials of formula (VI), wherein W' is halo, can easily be derived from an 1-Ar-2-haloethanone by reacting the latter with a 1,2,3-propanetriol according to the procedures described hereinabove for the preparation of (1) starting from (IX) and (X) and converting the free hydroxy group of the thus obtained intermediate into a reactive ester thereof according to methodologies generally known in the art.

Starting materials of formula (IX) can conveniently be prepared by reacting 1-Ar-2-haloethanone with an azole, (VIII), in an inert solvent, if appropriate in the presence of a base.

Starting materials of formula (X) can conveniently be prepared by O-alkylating compounds of formula (V) with a 3-halo-1,2-propanediol according to the procedures described hereinabove for the preparation of (I) starting from (IV) and (V).

The previously described intermediates and starting materials may also be converted into each other following art-known functional group transformation procedures.

The compounds of formula (I), the pharmaceutically acceptable acid addition salts and stereochemically isomeric forms thereof are useful agents due to their favourable anti-microbial properties and particularly to their increased solubility. The strong anti-microbial activity of the compounds of formula (I) can be demonstrated for example, in the "Oral treatment of vaginal candidosis in rats" test or in the "Topical treatment of vaginal candidosis in rats" test illustrating the useful anti-microbial activity of the compounds of the present invention.

In view of their useful anti-microbial activity, the subject compounds may be formulated into various pharmaceutical forms for administration purposes.

To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of formula (I), the pharmaceutically acceptable acid addition salts and stereochemically isomeric forms thereof are useful agents in combatting fungi and bacteria. For example, said compounds are found to be highly active against a wide variety of fungi such as, for example, *Microsporum canis, Pityrosporum ovale, Ctenomyces mentagrophytes, Trichophyton rubrum, Phialophora verrucosa, Cryptococcus neoformans, Candida tropicalis, Candida albicans, Mucor species, Aspergillus fumigatus, Sporotricum schenckii* and *Saprolegnia species,* and against bacteria such as, for example, *Erysipelotrix insidiosa,* Staphylococci such as *Staphylococcus hemolyticus* and Streptococci such as *Streptococcus pyogenes.* In view of their potent, local as well as systemic, anti-microbial activity the compounds of this invention constitute useful tools for the destruction or prevention of the growth of fungi and bacteria and more particularly they can effectively be used in the treatment of subjects suffering from such microorganisms.

Those of skill in treating warm-blooded animals suffering from diseases caused by fungi and/or bacteria could easily determine the effective amount from the test results presented here. In general it is contemplated that an effective amount would be from 0.01 mg/kg to 50 mg/kg body weight, and more preferably from 0.05 mg/kg to 20 mg/kg body weight.

The following examples are intended to illustrate and not to limit the scope of the present invention. Unless otherwise stated all parts therein are by weight.

EXPERIMENTAL PART

A. Preparation of intermediates

EXAMPLE 1

(a) A mixture of 200 parts of 1,2,3-propanetriol, 90 parts of 1-(2,4-difluorophenyl)-2-(1H-1,2,4-triazol-1-yl)ethanone, 600 parts of methanesulfonic acid and 190 parts of benzene was stirred first at reflux for 3 hours using a water-separator and further overnight at room temperature. The reaction mixture was added dropwise to a sodium hydrogen carbonate solution. The product was extracted with trichloromethane. The extract was washed with water, dried, filtered and evaporated. The residue was triturated in 4-methyl-2-pentanone. The product was filtered off and dried, yielding 80 parts (67.2%) of (cis+trans)-2-(2,4-difluorophenyl)-2-(1H-1,2,4-triazol-1-ylmethyl)-1,3-dioxolane-4-methanol (intermediate 1).

(b) A mixture of 69 parts of 3,5-dinitrobenzoyl chloride, 80 parts of (cis+trans)-2-(2,4-difluorophenyl)-2-(1H-1,2,4-triazol-1-ylmethyl)-1,3-dioxolane-4-methanol, 400 parts of pyridine and 520 parts of dichloromethane was stirred for 3 hours at room temperature. The reaction mixture was evaporated and the residue was taken up in water. The product was extracted with trichloromethane. The extract was dried, filtered and evaporated. The residue was purified by column chromatography over silica gel using a mixture of trichloromethane and methanol (99:1 by volume) as eluent. The pure fractions were collected and the eluent was evaporated, yielding 90 parts (70.4%) of (cis)-2-(2,4-difluorophenyl)-2-(1H-1,2,4-triazol-1-ylmethyl)-1,3-dioxolane-4-methanol 3,5-dinitrobenzoate(ester) as a residue (intermediate 2).

(c) A mixture of 90 parts of (cis)-2-(2,4-difluorophenyl)-2-(1H- 1,2,4-triazol-1-ylmethyl)-1,3-dioxolane-4-methanol 3,5-dinitrobenzoate (ester), 16 parts of sodium hydroxide solution 50%, 800 parts of 1,4-dioxane and 400 parts of water was stirred overnight at room temperature. The reaction mixture was poured into water. The product was extracted with dichloromethane. The extract was washed with water, dried, filtered and evaporated. The residue was triturated in 4-methyl-2-pentanone. The product was filtered off and dried, yielding 30 parts (56.0%) of cis-2-(2,4-difluorophenyl)-2-(1H-1,2,4-triazol-1-ylmethyl)-1,3-dioxolane-4-methanol as a residue (intermediate 3).

(d) A mixture of 11.4 parts of methanesulfonyl chloride, 25 parts of cis-2-(2,4-difluorophenyl)-2-(1H-1,2,4-triazol-1-ylmethyl)-1,3-dioxolane-4-methanol, 300 parts of pyridine and 390 parts of dichloromethane was stirred for 3 hours at room temperature. The reaction mixture was evaporated. The residue was taken up in trichloromethane. The organic phase was dried, filtered and evaporated. The residue was triturated in 2,2'-oxybispropane. The product was filtered off and dried, yielding 29.4 parts (93.2%) of cis-2-(2,4-difluorophenyl)-2-(1H-1,2,4-triazol-1-ylmethyl)-1,3-dioxolane-4-methanol methanesulfonate(ester) as a residue (intermediate 4).

In a similar manner there was also prepared: cis-2-(2,4-difluorophenyl)-2-(1H-imidazol-1-ylmethyl)-1,3-dioxolane-4methanol methanesulfonate(ester) ethanedioate(1:1) as a residue (intermediate 5).

EXAMPLE 2

(a) 270 Parts of benzene and 1332 parts of methanesulfonic acid were dissolved azeotropically and then a mixture of 108.4 parts of 1-(4-fluorophenyl)-2-(1H-1,2,4-triazol-1-yl)ethanone and 243 parts of 1,2,3-propanetriol was added. After stirring for 2 hours at reflux temperature, using a water separator, the reaction mixture was added dropwise in 1000 parts of a mixture of ammonium hydroxide, crushed ice and dichloromethane. The product was extracted with dichloromethane. The extract was washed with water, dried, filtered and evaporated. The residue was stirred in 2,2'-oxybispropane. The product was filtered off and dried, yielding 151 parts (96.5%) of (cis+trans)-2-(4-fluorophenyl)-2-(1H-1,2,4-triazol-1-ylmethyl)-1,3-dioxolane-4-methanol (intermediate 6).

(b) A mixture of 6.8 parts of 2-naphthalenesulfonyl chloride, 5.5 parts of (cis+trans)-2-(4-fluorophenyl)-2-(1H-1,2,4-triazol-1-ylmethyl)-1,3-dioxolane-4-methanol, 14 parts of N,N-diethylethanamine, 1 part of ethyl acetate and 150 parts of N,N-dimethyl-4-pyridinamine was stirred for 2 hours at room temperature. The reaction mixture was filtered. The filtrate was washed with water, dried, filtered and evaporated. The residue was filtered over silica gel using trichloromethane as eluent. The pure fractions were collected and the eluent was evaporated. The residue was further purified by column chromatography over silica gel using a mixture of trichloromethane and methanol (98:2 by volume) as eluent. The pure fractions were collected and the eluent was evaporated. The residue was crystallized from 4-methyl-2-pentanone. The product was filtered off and dried, yielding 0.7 parts (7.4%) of cis-[[2-(4-fluorophenyl)-2-(1H-1,2,4-triazol-1-ylmethyl)-1,3-dioxolan-4-yl]methyl] 2-naphthalenesulfonate; mp. 125.4° C. (intermediate 7).

In a similar manner there was also prepared: cis-[[2-(2,4-difluorophenyl)-2-(1H-1,2,4-triazol-1-ylmethyl)-1,3-dioxolan-4-yl]methyl]2-naphthalenesulfonate; mp. 139.5° C. (intermediate 8).

EXAMPLE 3

(a) A mixture of 91.7 parts of 4-(1-piperazinyl)phenol, 71.0 parts of 1-fluoro-4-nitrobenzene, 60.0 parts of potassium carbonate and 450 parts of N,N-dimethylacetamide was stirred over weekend at room temperature. Water was added and after standing for 5 hours, the product was filtered off. It was purified by column chromatography over silica gel using trichloromethane as eluent. The pure fractions were collected and the eluent was evaporated, yielding 114.4 parts (76%) of 4-[4-(4-nitrophenyl)-1-piperazinyl]phenol; mp. 260.0° C. (intermediate 9).

(b) A mixture of 9.0 parts of 4-[4-(4-nitrophenyl)-1-piperazinyl]phenol, 13.6 parts of cis-2-(2,4-difluorophenyl)-2-(1H-1,2,4-triazol-1-ylmethyl)-1,3-dioxolane-4-methanol methanesulfonate(ester), 6.0 parts of potassium hydroxide and 90 parts of N,N-dimethylformamide was stirred overnight at 70° C. under nitrogen atmosphere. After cooling, the reaction mixture was diluted with water. The precipitated product was filtered off and purified by column chromatography over silica gel using a mixture of trichloromethane, ethyl acetate, hexane and methanol (500:300:200:0.5 by volume) as eluent. The pure fractions were collected and the eluent was evaporated. The residue was crystallized from 4-methyl-2-pentanone. The product was filtered off and dried, yielding 6.69 parts (38.5%) of cis-1-[4-[[2-(2,4-difluorophenyl)-2-(1H-1,2,4-triazol-1-ylmethyl)-1,3-dioxolan-4-yl]methoxy]phenyl]-4-(4-nitrophenyl)-piperazine: mp. 169.8° C. (intermediate 10).

(c) A mixture of 38.3 parts of cis-1-[4-[[2-(2,4-difluorophenyl)-2-(1H-1,2,4-triazol-1-ylmethyl)-1,3-dioxolan-4-yl]methoxy]phenyl]-4-(4-nitrophenyl)piperazine, 2 parts of a solution of thiophene in methanol 4% and 600 parts of 2-methoxyethanol was hydrogenated at normal pressure and at 50° C. with 2 parts of platinum-on-charcoal catalyst 5%. After the calculated amount of hydrogen was taken up, the catalyst was filtered off while hot and the filtrate was saturated with water. After cooling, the precipitated product was filtered off, washed with water and 2-propanol and crystallized from 1,4-dioxane. The product was filtered off and dried, yielding 22.7 parts (62.6%) of cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]benzenamine; mp. 193.0° C. (intermediate 11).

(d) To a stirred solution of 81.9 parts of cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]benzenamine and 2.0 parts of N,N-dimethyl-4-pyridinamine in 200 parts of pyridine were added dropwise 37.7 parts of phenyl carbonochloridate during 15 minutes. Upon completion, stirring was continued overnight at room temperature. On the addition of 700 parts of Water, the crystallized product was isolated, washed successively with water, 2-propanol and 2,2'-oxybispropane and chromatographed on a silica gel column with a mixture of trichloromethane and methanol (98.5:1.5 by volume) as eluent. After trituration With 4-methyl-2-pentanone, the product was filtered off, yielding 4.7 parts (5%) of Phenyl cis-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]carbamate; mp. 178.1° C. (intermediate 12).

(e) A mixture of 27.7 parts of methyl 2-methylalanine hydrochloride, 98.5 parts of phenyl cis-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-carbamate. 20.0 parts of sodium hydrogen carbonate and 300 parts of 1,4-dioxane was stirred overnight at reflux temperature. Water was added till crystallization occured and the whole was refluxed for 2 hours. After cooling, the precipitated product was filtered off and purified by column chromatography over silica gel using a mixture of trichloromethane and methanol (98:2 by volume) as eluent. The pure fractions were collected and the eluent was evaporated. The residue was crystallized from 4-methyl-2-pentanone. The product was filtered off and dried, yielding 35.3 parts (36.4%) of cis-3-[4-[4-[4-[[2-(2,4-difluorophenyl)-2-(1H-1,2,4-triazol-1-yl-methyl)-1,3-dioxolan-4-yl]methoxy]-phenyl]-1-piperazinyl]phenyl]-5,5-dimethyl-2,4-imidazolidinedione; mp. 211.8° C. (intermediate 13).

EXAMPLE 4

A mixture of 25 parts of ethyl [(dimethylamino)methylene]hydrazinecarboxylate, 58 parts of cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]benzenamine and 75.6 parts of tetrahydrothiophene 1,1-dioxide was stirred for 3 hours at 160° C. (oil bath). 80 Parts of 4-methyl-2-pentanone were added. After cooling, the precipitated product was filtered off, washed with 4-methyl-2-pentanone and dried, yielding 46.2 parts (70%) of cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]-phenyl]-2,4-dihydro-3H-1,2,4-triazol-3-one as a residue (intermediate 14).

Example 5

(a) To a stirred mixture of 75.6 parts of carbon disulfide, 30 parts of N,N'-methanetetraylbis[cyclohexanamine]and 200 parts of pyridine were added portionwise 70 parts of cis-4-[4-[4-[2-(2,4-dichlorophenyl)-2-(1H-1,2,4-triazol-1-ylmethyl)-1,3-dioxolan-4-ylmethoxy]-phenyl]-1-piperazinyl]benzenamine. Upon completion, stirring was continued for 3 hours at room temperature. 210 Parts of 2,2'-oxybispropane were added whereupon the product was precipitated. It was filtered off, washed with 2-propanol and triturated twice in 2-propanol. The product was filtered off and dissolved in trichloromethane. The solution was filtered over silica gel using a mixture of trichloromethane and methanol (99:1 by volume) as eluent. The pure fractions were collected and the eluent was evaporated. The residue was crystallized from ethyl acetate, yielding 3.2 parts of cis-1-[4-[[2-(2,4-dichlorophenyl)-2-(1H-1,2,4-triazol-1-ylmethyl)-1,3-dioxolan-4-yl]methoxy]phenyl]-4-(4-isothiocyanatophenyl)piperazine; mp. 149.1 (intermediate 15).

(b) A mixture of 1.5 parts of 2-aminoethanol, 11.5 parts of cis-1-[4-[[2-(2,4-dichlorophenyl)-2-(1H-1,2,4-triazol-1-ylmethyl)-1,3-dioxolan-4-yl]methoxy]phenyl]-4-(4-isothiocyanatophenyl)piperazine and 130 parts of dichloromethane was stirred for 1 hour at room temperature. After evaporation, the residue was boiled in 2-propanone. After cooling, the product was filtered off and dried, yielding 11.9 parts (96.5%) of cis-N-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N'-(2-hydroxyethyl)thiourea: mp. 181.0° C. (intermediate 16).

(c) A solution of 7.2 parts of thionyl chloride in 75 parts of trichloromethane was stirred in an ice-cold bath. A suspension of 10.9 parts of cis-N-[4-[4-[4-[[2-(2.4-dichlorophenyl)-2-(1H-1,2,4-triazol-1-ylmethyl)-1,3-dioxolan-4-yl]methoxy]phenyl]-1-piperazinyl]-phenyl]-N'-(2-hydroxyethyl)thiourea in 375 parts of trichloromethane was added dropwise to the mixture at 0° C. The reaction mixture was allowed to reach room temperature and the whole was stirred for 1 hour at reflux temperature. After cooling, the mixture was neutralized with a sodium hydrogen carbonate solution in water and 80 parts of methanol were added. The whole was stirred till all solid entered the solution. The separated organic layer was evaporated and the residue was purified twice by column chromatography over silica gel: first using a mixture of trichloromethane and methanol (99:1 by volume) and then a mixture of trichloromethane, methanol, ethyl acetate and hexane (49:1:30:20 by volume) as eluents. The pure fractions were collected and the eluent was evaporated. The residue was crystallized from 2-propanone. The product was filtered off and dried, yielding 3.5 parts (33.0%) of cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(2-thiazolidinylidene)benzenamine; mp. 179.6° C. (intermediate 17).

Example 6

(a) A mixture of 6 parts of 4-[4-(4-methoxyphenyl)-1-piperazinyl]benzenamine, 3.6 parts of phenyl carbonochloridate, 75 parts of pyridine and 98 parts of dichloromethane was stirred and warmed till all solid entered solution. Stirring was continued for 30 minutes at room temperature. The reaction mixture was poured into 500 parts of water and 210 parts of 2,2'-oxybispropane were added. The whole was stirred for a while. The precipitated product was filtered off and crystallized from 1-butanol, yielding 5.2 parts (61%) of phenyl [4-[4-(4-methoxyphenyl)-1-piperazinyl]phenyl]carbamate; mp. 204.5 (intermediate 18).

(b) A mixture of 23 parts of methyl 2-methylalanine hydrochloride, 55 parts of phenyl [4-[4-(4-methoxyphenyl)-1-piperazinyl]phenyl]carbamate, 12.45 parts of sodium hydrogen carbonate, 10 parts of N,N-dimethyl-4-pyridinamine and 300 parts of 1,4-dioxane was stirred overnight at reflux temperature. Water was added till saturation. After stirring for another hour at reflux temperature, the mixture was cooled to room temperature. The product was filtered off, washed with water and 2,2'-oxybispropane and purified by column chromatography over silica gel using a mixture of trichloromethane and methanol (98:2 by volume) as eluent. The pure fractions were collected and the eluent was evaporated. The residue was crystallized from 4-methyl-2-pentanone. The product was filtered off and dried, yielding 45.33 parts (84.4%) of 3-[4-[4-(4-methoxyphenyl)-1-piperazinyl]phenyl]-5,5-dimethyl-2,4-imidazolidinedione; mp. 255.0° C. (intermediate 19).

(c) A mixture of 21.3 parts of 3-[4-[4-(4-methoxyphenyl)-1-piperazinyl]phenyl]-5,5-dimethyl-2,4-imidazolidinedione, 7.5 parts of 3-chloro-2-butanone, 6.0 parts of potassium carbonate and 180 parts of N,N-dimethylformamide was stirred overnight at 100° C. After cooling, the reaction mixture was diluted with 700 parts of water. The crystallized product was filtered off and purified by column chromatography over silica gel using a mixture of trichloromethane and methanol (98.5:1.5 by volume) as eluent. The pure fractions were collected and the eluent was evaporated. After trituration of the residue in methanol, the product was filtered off and crystallized from 4-methyl-2-pentanone, yielding 7.77 parts (30.9%) of 3-[4-[4-(4-methoxyphenyl)-1-piperazinyl]phenyl]-5,5-dimethyl-1-(1-methyl-2-oxopropyl)-2,4-imidazolidinedione; mp. 225.9° C. (intermediate 20).

(d) A mixture of 25.6 parts of 3-[4-[4-(4-methoxyphenyl)-1-piperazinyl]phenyl]-5,5-dimethyl-1-(1-methyl-2-oxopropyl)-2,4-imidazolidinedione, 3 parts of sodium disulfite and 375 parts of a hydrobromic acid solution 48% in water was stirred for 6 hours at reflux temperature. After cooling. the crystallized product was filtered off, washed with 2-propanone and suspended in a mixture of water, trichloromethane and 1-butanol. The whole was treated with potassium carbonate (pH 8~9). The separated organic layer was set aside and the aqueous phase was extracted twice with the same mixture. The combined extracts (see above) were evaporated in vacuo. The residue was crystallized from 1-butanol. The product was filtered off and dried, yielding 21.3 parts (86%) of 3-[4-[4-(4-hydroxyphenyl)-1-piperazinyl]phenyl]-5,5-dimethyl-1-(1-methyl-2-oxopropyl)-2,4-imidazolidinedione; mp. 225.9° C. (intermediate 21).

Following the same procedure and using equivalent amounts of the appropriate starting materials, there were also prepared:

2,4-dihydro-4-[4-[4-(4-hydroxyphenyl)-1-piperazinyl]phenyl]-2-(1-methyl-2-oxopropyl)-3H-1,2,4-triazol-3-one; mp. 192.2° C. (intermediate 22);

2-[2-(4-fluorophenyl)-1-methyl-2-oxoethyl]-2,4-dihydro-4-[4-[4-(4-hydroxyphenyl)-1-piperazinyl]phenyl]-3H-1,2,4-4-triazol-3-one; mp. 215.1° C. (intermediate 23);

2,4-dihydro-4-[4-[4-(4-hydroxyphenyl)-1-piperazinyl]phenyl]-2-(1-methyl-2-oxo-2-phenylethyl)-3H-1,2,4-triazol-3-one: mp. 249.3° C. (intermediate 24);

2-[2-(4-bromophenyl)-1-methyl-2-oxoethyl]-2,4-dihydro-4-[4-[4-(4-hydroxyphenyl)-1-piperazinyl]phenyl]-3H-1,2,4-triazol-3-one; mp. 211.1° C. (intermediate 25);

In a similar manner there are also prepared:

2,4-dihydro-4-[4-[4-(4-hydroxyphenyl)-1-piperazinyl]phenyl]-2-(2-oxocyclopentyl)-3H-1,2,4-triazol-3-one; (intermediate 26); and 2,4-dihydro-4-[4-[4-(4-hydroxyphenyl)-1-piperazinyl]phenyl]-2-(2-oxocyclohexyl)-3H-1,2,4-triazol-3-one; (intermediate 27).

EXAMPLE 7

A mixture of 9.7 parts of 1-[2-(1-methylethoxy)ethyl]-3-[4-[4-(phenylmethoxy)phenyl]-1-piperazinyl]phenyl]-2-imidazolidinone and 250 parts of acetic acid was hydrogenated at normal pressure and at 50° C. with 2 parts of palladium-on-charcoal catalyst 10%. After the calculated amount of hydrogen was taken up, the catalyst was filtered off and the filtrate was evaporated. The residue was dissolved in a mixture of methanol and water and the whole was neutralised with a sodium hydrogen carbonate solution. The precipitated product was filtered off and crystallized from 4-methyl-2-pentanone. The product was filtered off and dried at 100° C., yielding 6.3 parts (76.8%) of 1-[4-[4-(4-hydroxyphenyl)-1-piperazinyl]phenyl]-3-[2-(1-methylethoxy)ethyl]-2-imidazolidinone hemihydrate; mp. 178.3° C. (intermediate 28).

In a similar manner there was also prepared: 1-[4-[4-(4-hydroxyphenyl)-1-piperazinyl]phenyl]-3-(1-methyl-2-oxopropyl)-2-imidazolidinone; mp. 196.6° C. (intermediate 29);

B. PREPARATION OF FINAL COMPOUNDS

EXAMPLE 1

A mixture of 2.8 parts of 1-bromo-4-(2-bromoethoxy)benzene, 5 parts of cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-3-H1,2,4-triazol-3-one, 0.7 parts of potassium hydroxide and 100 parts of dimethyl sulfoxide was stirred for 4 hours at room temperature. The reaction mixture was poured into water. The product was extracted with dichloromethane. The extract was subsequently washed with water, dried, filtered and evaporated. The residue was purified by column chromatography over silica gel usinq a mixture of trichloromethane and methanol (99:1 by volume) as eluent. The pure fractions were collected and the eluent was evaporated. The residue was crystallized from a mixture of 2-propanone and 2,2'-oxybispropane. The product was filtered off and recrystallized from methylbenzene, yielding 5.2 parts (79%) of cis-2-[2-(4-bromophenoxy)ethyl]-4-[4-[4-[[2-(2,4-dichlorophenyl)-2-(1 H-1,2,4-triazol-1-ylmethyl)-1,3-dioxolan-4- yl]methoxy]phenyl]-1-piperazinyl]phenyl]-2,4-dihydro-3H-1,2,4-triazol-3-one; mp. 143.3° C. (compound 1). In a similar manner there were also prepared:

tracted with dichloromethane. The extract was subsequently washed with water, dried, filtered and evaporated. The residue was purified by filtration over silica

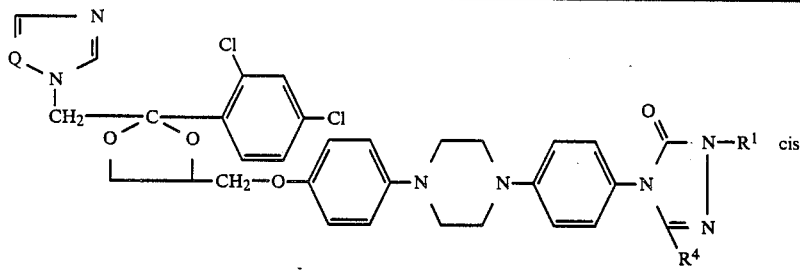

| No. | $R^1$ | $R^4$ | Q | base/salt | mp. (°C.) |
|---|---|---|---|---|---|
| 2 | $C_2H_5-O-C_2H_4$ | H | CH | base | 151.1 |
| 3 | $C_2H_5-O-C_2H_4$ | $CH_3$ | CH | base | 123.3 |
| 4 | $C_2H_5-S-C_2H_4$ | H | CH | base | 205.9 |
| 5 | $C_2H_5-O-C_2H_4$ | H | N | base | 165 |
| 6 | $CH_3-O-C_2H_4$ | H | N | base | 164 |
| 7 | $C_6H_5-O-C_2H_4$ | H | N | $H_2O$ | 158.1 |
| 8 | $C_6H_5-O-C_2H_4$ | $CH_3$ | CH | base | 160.8 |
| 9 | $C_6H_5-O-C_2H_4$ | $CH_3$ | N | base | 145.3 |
| 10 | $C_6H_5-O-C_2H_4$ | H | CH | base | 150.6 |
| 11 | $4-Br-C_6H_4-O-C_2H_4$ | $CH_3$ | CH | base | 149.8 |
| 12 | $4-Br-C_6H_4-O-C_2H_4$ | H | CH | base | 151.0 |
| 13 | $4-Br-C_6H_4-O-C_2H_4$ | $CH_3$ | N | base | 116.5 |
| 14 | $2-Cl-C_6H_4-O-C_2H_4$ | H | CH | base | 153.7 |
| 15 | $2-Cl-C_6H_4-O-C_2H_4$ | $CH_3$ | CH | base | 150.5 |
| 16 | 1,3-dioxolan-2-yl-$CH_2$ | H | CH | base | 194.1 |
| 17 | $2-Cl-C_6H_4-O-C_2H_4$ | H | N | base | 141.3 |
| 18 | $2-Cl-C_6H_4-O-C_2H_4$ | $CH_3$ | N | base | 147.4 |
| 19 | $C_2H_5-O-C_2H_4$ | $CH_3$ | N | base | 122.4 |

EXAMPLE 2

A mixture of 1.6 parts of (2-chloroethoxy)cyclohexane, 5 parts of cis-4-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2,4-dihydro-5-methyl-3H-1,2,4-triazol-3-one, 0.4 parts of a sodium hydride dispersion 50% and 100 parts of dimethyl sulfoxide was stirred for 5 hours at 80° C. The reaction mixture was cooled and poured into water. The product was extracted with dichloromethane. The extract was subsequently washed with water, dried, filtered and evaporated. The residue was purified by filtration over silica gel using a mixture of trichloromethane and methanol (99.5:0.5 by Volume) as eluent. The filtrate was evaporated and the residue was crystallized from 4-methyl-2-pentanone, yielding 4.1 parts (69%) of cis-2-[2-(cyclohexyloxy)ethyl]-4-[4-[4-[4-[[2-(2,4-dichlorophenyl)-2-(1-Himidazol-1-yl-methyl)-1.3-dioxolan-4-yl]methoxy]-phenyl]-1-piperazinyl]phenyl]-2.4-dihydro-5-methyl-3H-1,2,4-triazol-3-one; mp. 160.2° C. (compound 20).

In a similar manner there were also prepared:

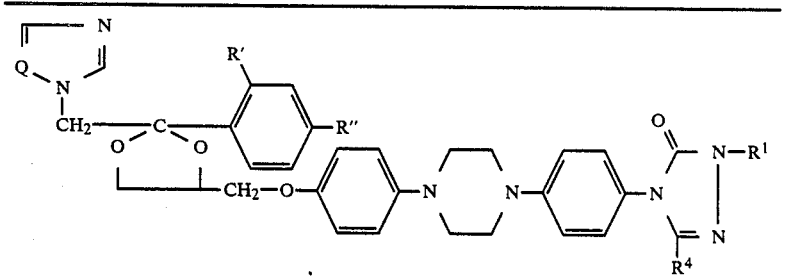

| No. | $R^1$ | $R^4$ | Q | R' | R'' | base/salt | mp. (°C.) |
|---|---|---|---|---|---|---|---|
| 21 | $C_2H_5-O-CH_2$ | H | CH | Cl | Cl | base | 140.4 |
| 22 | $CH_3-O-CH_2$ | $CH_3$ | CH | Cl | Cl | base | 180.9 |
| 23 | $C_2H_5-O-CH_2$ | $CH_3$ | CH | Cl | Cl | base | 136.0 |
| 24 | $CH_3-O-CH_2$ | H | CH | Cl | Cl | base | 165 |
| 25 | $CH_3-O-CH_2$ | $CH_3$ | N | Cl | Cl | $H_2O$ | 148 |
| 26 | $C_2H_5-O-CH_2$ | $CH_3$ | N | Cl | Cl | base | 133.2 |
| 27 | $C_2H_5-S-C_2H_4$ | H | N | Cl | Cl | base | 177.9 |
| 28 | $C_2H_5-O-CH_2$ | H | N | Cl | Cl | Base | 137.7 |
| 29 | $CH_3-O-CH_2$ | H | N | Cl | Cl | base | 171.3 |
| 30 | $C_2H_5-S-C_2H_4$ | $CH_3$ | N | Cl | Cl | $H_2O$ | 111.4 |
| 31 | $CH_3-O-C_2H_4$ | $CH_3$ | CH | Cl | Cl | base | 156.1 |
| 32 | $CH_3-O-C_2H_4$ | $CH_3$ | N | Cl | Cl | $H_2O$ | 107.5 |
| 33 | $CH_3-O-C_2H_4$ | H | CH | Cl | Cl | base | 142.3 |
| 34 | $(C_2H_5-O)_2C_2H_3$ | H | CH | Cl | Cl | base | 141.9 |
| 35 | 1,3-dioxolan-2-yl-$CH_2$ | H | N | Cl | Cl | base | 194.8 |

-continued

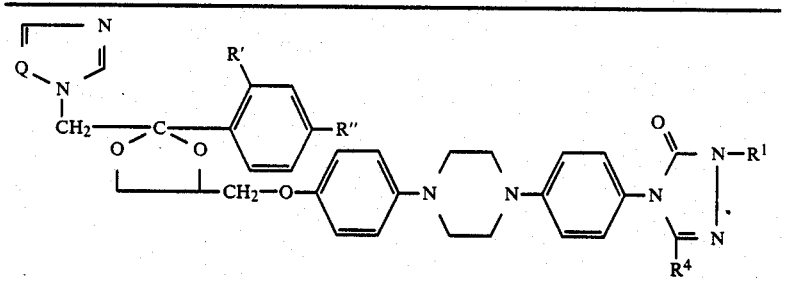

| No. | R¹ | R⁴ | Q | R' | R'' | base/salt | mp. (°C.) |
|---|---|---|---|---|---|---|---|
| 36 | 1,3-dioxolan-2-yl-CH₂ | CH₃ | N | Cl | Cl | base | 169.5 |
| 37 | (CH₃—O)₂C₂H₃ | CH₃ | CH | Cl | Cl | base | 157.3 |
| 38 | 1,3-dioxolan-2-yl-CH₂ | CH₃ | CH | Cl | Cl | base | 195.6 |
| 39 | (C₂H₅—O)₂C₂H₃ | CH₃ | N | Cl | Cl | base | 162.0 |
| 40 | (C₂H₅—O)₂C₂H₃ | H | N | Cl | Cl | base | 150.5 |
| 41 | (C₂H₅—O)₂C₂H₃ | CH₃ | CH | Cl | Cl | base | 173.2 |
| 42 | (CH₃—O)₂C₂H₃ | H | CH | Cl | Cl | base | 153.5 |
| 43 | (CH₃)₂CH—O—C₂H₄ | H | CH | Cl | Cl | base | 182.5 |
| 44 | (CH₃)₂CH—O—C₂H₄ | H | N | Cl | Cl | base | 152.0 |
| 45 | (CH₃)₂CH—O—C₂H₄ | CH₃ | N | Cl | Cl | base | 146.1 |
| 46 | (CH₃)₂CH—O—C₂H₄ | CH₃ | CH | Cl | Cl | base | 142.8 |
| 47 | tetrahydrofuran-3-yl-CH₂ | H | N | Cl | Cl | base | 176.6 |
| 48 | tetrahydrofuran-3-yl-CH₂ | H | CH | Cl | Cl | base | 185~200 |
| 49 | n.C₃H₇—O—C₂H₄ | H | CH | Cl | Cl | base | 171.2 |
| 50 | n.C₃H₇—O—C₂H₄ | CH₃ | CH | Cl | Cl | base | 148.3 |
| 51 | n.C₃H₇—O—C₂H₄ | CH₃ | N | Cl | Cl | base | 145.5 |
| 52 | tetrahydrofuran-3-yl-CH₂ | CH₃ | CH | Cl | Cl | base | 157.7 |
| 53 | n.C₃H₇—O—C₂H₄ | H | N | Cl | Cl | base | 141.7 |
| 54 | tetrahydrofuran-3-yl-CH₂ | CH₃ | N | Cl | Cl | base | 144.9 |
| 55 | cyclohexyl-O—C₂H₄ | H | CH | Cl | Cl | base | 165.2 |
| 56 | cyclohexyl-O—C₂H₄ | H | N | Cl | Cl | base | 168.8 |
| 57 | cyclohexyl-O—C₂H₄ | CH₃ | N | Cl | Cl | base | 145.8 |
| 58 | CH₃—O—(CH₃)CH | H | N | F | F | base | 141.2 |

EXAMPLE 3

A mixture of 5 parts of cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-3H-1,2,4-triazol-3-one, 0.42 parts of a sodium hydride dispersion 50%, 100 parts of dimethyl sulfoxide and 18 parts of methylbenzene was stirred for 1 hour at 59° C. After cooling to room temperature, 0.62 parts of chloromethoxymethane were added and stirring was continued for 1 hour. The reaction mixture was poured into water and the product was extracted with dichloromethane. The extract was washed with water, dried and filtered over silica gel using a mixture of trichloromethane and methanol (99:1 by volume) as eluent. The pure fractions were collected and the eluent was evaporated. The residue was crystallized from 4-methyl-2-pentanone. The product was filtered off and dried, yielding 2.9 parts (54%) of cis-4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-(methoxymethyl)-3H-1,2,4-triazol-3-one; mp. 154.9° C. (compound 59).

EXAMPLE 4

A mixture of 5 parts of cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-5-methyl-3H-1,2,4-triazol-3-one, 0.4 parts of a sodium hydride dispersion 50% and 100 parts of dimethyl sulfoxide was stirred at 80° C. till foaming had ceased. Then there were added 5 parts of 2-chloro-1,1-dimethoxyethane and 0.1 parts of potassium iodide and the whole was stirred for 4 hours at 120° C. The reaction mixture was cooled and poured into water. The product was extracted with dichloromethane. The extract was washed with water, dried, filtered and evaporated. The residue was purified by column chromatography over silica gel using a mixture of trichloromethane and methanol (99:1 by volume) as eluent. The pure fractions were collected and the eluent was evaporated. The residue was crystallized from 4-methyl-2-pentanone. The product was filtered off and dried at 140° C., yielding 2.9 parts (55%) of cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2-(2,2-dimethoxyethyl)-2,4-dihydro-5-methyl-3H-1,2,4-triazol-3-one; mp. 155.2° C. (compound 60).

In a similar manner there was also prepared: cis-4-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-2-(2,2-dimethoxyethyl)-2,4-dihydro-3H-1,2,4-triazol-3-one; mp. 167.1° C. (compound 61).

EXAMPLE 5

A mixture of 2.0 parts of 2-(3-bromopropoxy)tetrahydro-2H-pyran, 5.0 parts of cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]-phenyl]-2,4-dihydro-5-methyl-3H-1,2,4-triazol-3-one, 2.0 parts of potassium hydroxide and 45 parts of N,N-dimethylformamide was stirred for 6 hours at room temperature. Water was added. The product was extracted twice with dichloromethane. The combined extracts were washed with water, dried, filtered and evaporated in vacuo. The residue was taken up in methylbenzene and the whole was evaporated again. The residue was purified by column chromatography over silica gel using a mixture of trichloromethane and methanol (98:2 by volume) as eluent. The pure fractions were collected and the eluent was evaporated. The residue was triturated in methanol. The product was filtered off and crystallized from methanol, yielding 14 parts (85%) of cis-4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-2.4-dihydro-5-methyl-2-[3-[(tetrahydro-2H-pyran-2-yl)oxy]propyl]-3H-1,2,4-triazol-3-one; mp. 94.5° C. (compound 62).

In a similar manner there were also prepared:

cis-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2-[(2.2-dimethyl-1,3-dioxolan-4-yl)methyl]-2,4-dihydro-3H-1,2,4-triazol-3-one; mp. 194.8° C. (compound 63);

cis-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2,4-dihydro-2-[3-[(tetrahydro-2H-pyran-2-yl)oxy]propyl]-3H-1,2,4-triazol-3-one; mp. 120.1° C. (compound 64);

cis-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2,4-dihydro-5-methyl-2-[2-[(tetrahydro-2H-pyran-2-yl)oxy]ethyl]-3H-1,2,4-triazol-3-one; mp. 135.6° C. (compound 65);

cis-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2,4-dihydro-5-methyl-2-[3-[(tetrahydro-2H-pyran-2-yl)oxy]propyl]-3H-1,2,4-triazol-3-one; mp. 144.8° C. (compound 66); and cis-4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2-(2-ethoxyethyl)-2,4-dihydro-3H-1,2,4-triazol-3-one; mp. 169.1° C. (compound 67).

EXAMPLE 6

A mixture of 7.6 parts of cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-5-methyl-3H-1,2,4-triazol-3-one, 0.7 parts of a sodium hydride dispersion 50% and 67.5 parts of N,N-dimethylformamide was stirred for 1 hour at 50° C. 3.1 Parts of 2,2-dimethyl-1,3-dioxolan-4-methanol methanesulfonate (ester) were added and the whole was stirred overnight at 50° C. After cooling, the reaction mixture was diluted with water. The product was extracted with dichloromethane. The extract was dried, filtered and evaporated in vacuo. The residue was purified by column chromatography over silica gel using a mixture of trichloromethane and methanol (98.5:1.5 by volume) as eluent. The pure fractions were collected and the eluent was evaporated. The residue was triturated in methanol. The product was filtered off and crystallized from 2-propanol, yielding 5.7 parts (64.2%) of cis-4-[4-[4-[[2-(2,4-dichlorophenyl)-2-(1H-1,2,4-triazol-1-ylmethyl)-1,3-dioxolan-4-yl]methoxy]-phenyl]-1-piperazinyl]phenyl]-2-[(2,2-dimethyl-1,3-dioxolan-4-yl)methyl]-2,4-dihydro-5-methyl-3H1,2,4-triazol-3-one; mp. 109.2° C. (compound 68).

In a similar manner there were also prepared:

cis-3-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-5,5-dimethyl-1-[2-[(tetrahydro-2H-pyran-2-yl)oxy]methyl]-2,4-imidazolidinedione; mp. 168.9° C. (compound 69);

cis-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2,4-dihydro-5-methyl-2-(1-methyl-2-oxopropyl)-3H-1,2,4-triazol-3-one; mp. 160.9° C. (compound 70);

cis-4-[4-[4-[[2-(2,4-dichlorophenyl)-2-(1H-imdazol-1-ylmethyl)-1,3-dioxolan-4-yl]methoxy]phenyl]-1-piperazinyl]phenyl]-2,4-dihydro-2-(1-methyl-2-oxopropyl)-3H-1,2,4-triazol-3-one; mp. 155.4° C. (compound 71);

cis-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2,4-dihydro-2-(2-oxopropyl)-3H-1,2,4-triazol-3-one; mp. 184.8° C. (compound 72); and cis-4-[4-[4-[[2-(2,4dichlorophenyl)-2-(1H-1,2,4triazol-1-yl-methyl)-1,3-dioxolan-4-yl]methoxy]phenyl]-1piperazinyl]phenyl]-2,4-dihydro-2-(1-methoxyethyl)-3H-1,2,4-triazol-3-one; mp. 178.5° C. (compound 73).

EXAMPLE 7

A mixture of 6.9 parts of cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-5,5-dimethyl-2,4-imidazolidinedione, 0.7 parts of a sodium hydride dispersion 50%, 90 parts of N,N-dimethylformamide and 27 parts of benzene was stirred for 1 hour at 40° C. Then there were added 3.0 parts of 2-(3-bromopropoxy)-tetrahydro-2H-pyran and stirring was continued overnight at 50° C. Water was added. The product was extracted twice with dichloromethane. The combined extracts were washed with water, dried, filtered and evaporated in vacuo. The residue was purified by column chromatography over silica gel using a mixture of trichloromethane and methanol (98.5:1.5 by volume) as eluent. The pure fractions were collected and the eluent was evaporated. The residue was triturated in methanol. The product was filtered off and dried, yielding 5.2 parts (62%) of cis-3-[4-[4-[4-[[2-(2,4--dichlorophenyl)-2-(1H-1,2,4-triazol-1-ylmethyl)-1,3-dioxolan-4-yl]methoxy]phenyl]-1-piperazinyl]phenyl]-5.5-dimethyl-1-[3-[(tetrahydro-2H-pyran-2-yl)oxy]-propyl]-2,4-imidazolidinedione; mp. 150.4° C. (compound 74).

In a similar manner there was also prepared:

cis-3-[4-[4-[4-[[2-(2,4-dichlorophenyl)-2-(1H-1,2,4-triazol-1-yl-methyl)-1.3-dioxolan-4-yl]methoxy]phenyl]-1-piperazinyl]phenyl]-1-[(2,2-dimethyl-1,3-dioxolan-4-yl)methyl]-5,5-dimethyl-2,4-imidazolidinedione; mp. 110.8° C. (compound 75).

EXAMPLE 8

A mixture of 1.6 parts of 3-chloro-2-butanone, 6.9 parts of cis-3-[4-[4-[4-[[2-(2,4-dichlorophenyl)-2-(1H-1,2,4-triaZol-1-yl-methyl)-1,3-dioxolan-4-yl]methoxy]-phenyl]-1-piperazinyl]phenyl]-5,5-dimethyl-2,4-imidazolidinedione, 2.0 parts of potassium carbonate and 90 parts of N,N-dimethylformamide was stirred overnight at 90° C. After cooling, water was added. The product was extracted three times with dichloromethane. The combined organic layers were evaporated in vacuo. The residue was purified by column chromatography over silica gel using a mixture of trichloromethane and methanol (98.5:1.5 by volume) as eluent. The pure fractions were collected and the eluent was evaporated. The residue was solidified in a mixture of 4-methyl-2-pentanone and 2,2'-oxybispropane. The product was triturated in methanol, yielding, after filtration and drying, 3.5 parts (46%) of cis-3-[4-[4-[4-[[2-(2,4-dichlorophenyl)-2-(1H1,2,4-triazol-1-ylmethyl)-1,3-dioxolan-4-yl]methoxy]phenyl]-1-piperazinyl]phenyl]-5,5-dimethyl-1-(1-methyl-2-oxopropyl)-2,4-imidazolidinedione; mp. 120.5° C. (compound 76).

EXAMPLE 9

A mixture of 2.4 parts of 3-chloro-2-butanone, 4 parts of cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(2-thiazolidinylidene) benzenamine, 5 parts of potassium carbonate, 135 parts of N,N-dimethylformamide and 90 parts of benzene was stirred for 8 hours at reflux temperature using a water separator. After cooling, the reaction mixture was poured into water and the layers were separated (the organic layer was set aside). The aqueous layer was extracted with ethylacetate. The extract was combined with the organic layer, which was set aside. The organic layer was washed with water, dried, filtered and evaporated. The residue was purified by column chromatography over silica gel using a mixture of trichloromethane and methanol (99:1 by volume) as eluent. The pure fractions were collected and the eluent was evaporated. The residue was crystallized from ethanol. The product was filtered off and dried, yielding 1.3 parts (29%) of cis-3-[2-[[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]imino]-3-thiazolidinyl]-2-butanone; mp. 146.3° C. (compound 77).

In a similar manner there were also prepared:
cis-4-[4-[4-[4-[[2-(2,4-difluorophenyl)-2-(1H-1,2,4-triazol-1-yl-methyl)-1.3-dioxolan-4-yl]methoxy]phenyl]-1-piperazinyl]phenyl]-2.4-dihydro-2-(2-methoxyethyl)-3H-1,2,4-triazol-3-one; mp. 169.5° C. (compound 78);
cis-3-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-5.5-dimethyl-1-(1-methyl-2-oxopropyl)-2.4-imidazolidinedione; mp. 154.5° C. (compound 79);
cis-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-(1-methyl-2-oxopropyl)-3H- 1,2,4-triazol-3-one; mp. 170.3° C. (compound 80);
cis-3-[4-[4-[4-[[2-(2,4-dichlorophenyl)-2-(1H-imidazol-1-yl-methyl)-1,3-dioxolan-4-yl]methoxy]phenyl]-1-piperazinyl]phenyl]-5,5-dimethyl-1-(1-methyl-2-oxopropyl)-2,4-imidazolidinedione; mp. 117.4° C. (compound 81);
cis-4-[4-[4-[4- [[2-(2,4-difluorophenyl,-2-(1H1,2,4-triazol-1-yl-methyl)-1,3-dioxolan-4-yl]methoxy]-phenyl]-1-piperazinyl]phenyl]-2,4-dihydro-2-[2-(1-methylethoxy)ethyl]-3H-1,2,4-triazol-3-one; mp. 169.9° C. (compound 82); and
cis-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-(2-propoxyethyl)-3H-1,2,4-triazol-3-one; mp. 147.8° C. (compound 83).

EXAMPLE 10

A mixture of 4.25 parts of 3-chloro-2-butanone, 6.5 parts of cis-4-[4-[4-[4-[[2-(2,4-dichlorophenyl)-2-(1H-1,2,4-triazol-1-yl-methyl)-1,3-dioxolan-4-yl]methoxy]-phenyl]-1-piperazinyl]phenyl]-2,4-dihydro-3H-1,2,4-triazol-3-one, 1.6 parts of sodium hydroxide and 18 parts of N,N-dimethylacetamide was stirred for 18 hours in an oil bath at 80° C. After cooling, another portion of 2.13 parts of 3-chloro-2-butanone and 0.8 parts of sodium hydroxide were added. The whole was stirred for 24 hours in an oil bath at 80° C. 40 Parts of water were added. The product was extracted with 375 parts of trichloromethane. The extract was washed with water, dried, filtered and evaporated. The residue was purified by column chromatography over silica gel using a mixture of trichloromethane and methanol (99:1 by volume) as eluent. The pure fractions were collected and the eluent was evaporated. The residue was boiled in 2-propanol and stirred overniqht at room temperature. The product was filtered off and dried in vacuo at 60° C. yelding a first fraction of 2.7 parts (37.5%) of cis-4-[4-[4-[[2-(2,4-dichlorophenyl)-2-(1H-1,2,4-triazol-1-ylmethyl)-1,3-dioxolan-4-yl]methoxy]-phenyl]-1-piperazinyl]-phenyl]-2,4-dihydro-2-(1-methyl-2-oxopropyl)-3H-1,2,4-triazol-3-one (compound 84). The less pure fractions were collected and the eluent was evaporated. The residue was stirred twice in water and the latter was decanted each time. 450 Parts of methylbenzene were added to the oily residue. The whole was washed twice with water. The organic layer was dried, filtered and evaporated. The residue was boiled in 2-propanol. After cooling, the product was filtered off and dried, yielding a second fraction of 1 part (14%) of cis-4-[4-[4-[[2-(2,4-dichlorophenyl)-2-(1H-1,2,4-triazol-1-ylmethyl)-1,3-dioxolan-4-yl]-methoxy]phenyl]-1-piperazinyl]phenyl]-2,4-dihydro-2-(1-methyl-2-oxopropyl)-3H-1,2,4-triazol-3-one (compound 84).

EXAMPLE 11

A mixture of 3 parts of butanoic acid anhydride, 4 parts of cis-3-[4-[4-[4-[[2-(2,4-dichlorophenyl)-2-(1H-imidazol-1-ylmethyl)-1,3-dioxolan-4-yl]methoxy]-phenyl]-1-piperazinyl]phenyl]-5,5-dimethyl-2,4-imidazolidinedione, 2 parts of N,N-dimethyl-4-pyridinamine and 130 parts of dichloromethane was stirred overnight at reflux temperature. After cooling, the whole was stirred with a sodium hydrogen carbonate solution. The organic layer was purified by column chromatography over silica gel using a mixture of trichloromethane and methanol (99:1 by volume) as eluent. The pure fractions were collected and the eluent was evaporated. The residue was crystallized from 2-propanol. The product was filtered off and dried, yielding 4.0 parts (90%) of cis-3-[4-[4-[4-[[2-(2,4-dichlorophenyl)-2-(1H-imidazol-1-yl-methyl)-1,3-dioxolan-4-yl]methoxy]phenyl]-1-piperazinyl]phenyl]-5,5-dimethyl--(1-oxobutyl)-2,4-imidazolidinedione; mp. 166.3° C. (compound 85). In a similar manner there were also prepared:

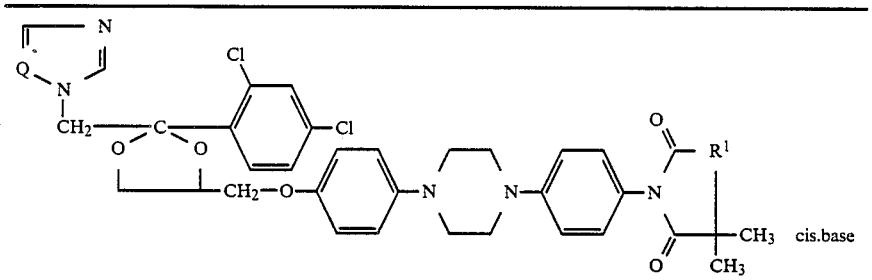

| No. | R¹ | Q | mp. (°C.) |
|-----|----|----|-----------|
| 86 | (CH₃)₂CH—CO | CH | 174.2 |
| 87 | CH₃—CO | CH | 124.3 |
| 88 | C₆H₅—CO | CH | 146.4 |
| 89 | C₂H₅—CO | CH | 110.7 |
| 90 | C₂H₅—CO | N | 206.0 |
| 91 | n-C₃H₇—CO | N | 195.8 |
| 92 | C₆H₅—CO | N | 152.7 |
| 93 | 4-Cl—C₆H₄—CO | CH | 138.8 |
| 94 | 4-Cl—C₆H₄—CO | N | 139.2 |

EXAMPLE 12

A mixture of 4 parts of 2-methylpropanoyl chloride, 4 parts of cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-5,5-dimethyl-2,4-imidazolidinedione, 4 parts of N,N-dimethyl-4-pyridinamine and 130 parts of dichloromethane was stirred for 2 hours at reflux temperature. 7 parts of N,N-diethylethanamine were added and the whole was stirred and refluxed for 1 hour. After cooling, the mixture was stirred with a sodium hydrogen carbonate solution. The layers were separated. The organic layer was filtered over silica gel using a mixture of trichloromethane and methanol (99:1 by volume). The pure fractions were collected and the eluent was evaporated. The residue was further purified by column chromatography over silica gel using a mixture of trichloromethane, methanol, ethyl acetate and hexane (49.5:0.5:30:20 by volume) as eluent. The second fraction was collected and the eluent was evaporated. The residue was crystallized from ethanol. The product was filtered off and dried, yielding 1.3 parts (29%) of cis-3-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]-phenyl]-5,5-dimethyl-1-(2-methyl-1-oxopropyl)-2,4-imidazolidinedione; mp. 110.2° C. (compound 95).

In a similar manner there was also prepared:
cis-1-acetyl-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-5,5-dimethyl-2,4-imidazolidinedione; mp. 213.2° C. (compound 96).

EXAMPLE 13

A mixture of 7.2 parts of 2,4-dihydro-4-[4-[4-(4-hydroxyphenyl)-1-piperazinyl]phenyl]-2-(1-methyl-2-oxo-2-phenylethyl)-3H-1,2,4-triazol-3-one, 8.9 parts of cis-[[2-(2,4-difluorophenyl)-2-(1H-1,2,4-triazol-1-ylmethyl)-1,3-dioxolan-4-yl]methyl]-2-naphthalenesulfonate, 1.0 part of sodium hydroxide pellets and 135 parts of N,N-dimethylformamide was stirred overnight at 55° C. under nitrogen atmosphere. After cooling the reaction mixture was diluted with water and 2 parts of acetic acid were added. The crystallized product was filtered off and dissolved in trichloromethane. The organic layer was dried, filtered and evaporated. The residue was purified by column chromatography over silica gel using a mixture of trichloromethane and methanol (98.5:1.5 by volume) as eluent. The pure fractions were collected and the eluent was evaporated. The residue was triturated in a mixture of 4-methyl-2-pentanone and 2.2'-oxybispropane. The precipitated product was filtered off and crystallized from 4-methyl- 2-pentanone. The product was filtered off and dried, yielding 1.4 parts (67%) of cis-4-[4-[4-[4-[[2-(2,4-difluorophenyl)-2-(1H-1,2,4-triazol-1-ylmethyl)-1,3-dioxolan-4-yl] -methoxy]phenyl]-1-piperazinyl]phenyl]-2,4-dihydro-2-(1-methyl-2-oxo-2-phenylethyl)-3H-1,2,4-triazol-3-one; mp. 129.1° C. (compound 97).

In a similar manner there were also prepared:
cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-[2-(4-fluorophenyl)-1-methyl-2-oxoethyl]-2,4-dihydro-3H-1,2,4-triazol-3-one; mp. 143.6° C. (compound 98);

cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methyl-2-oxo-2-phenylethyl)-3H-1,2,4-triazol-3-one ethanedioate(1:2); mp. 110.9° C. (compound 99);

cis-1-[4-[4-[4-[[2-(4-fluorophenyl)-2-(1H-1,2,4-triazol-1-ylmethyl)-1,3-dioxolan-4-yl]methoxy]phenyl]-1-piperazinyl]phenyl]-3-(1-methyl-2-oxopropyl)-2-imidazolidinone; mp. 162.9° C. (compound 100); and cis-2-[2-(4-bromophenyl)-1-methyl-2-oxoethyl]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-3H-1,2,4-triazol-3-one; mp. 171.9° C. (compound 101).

In a similar manner there are also prepared:
cis-1-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-3-[2-(1-methylethoxy)ethyl]-2-imidazolidinone (compound 102).

cis-4-[4-[4-[4-[[2-(2,4-difluorophenyl)-2-(1H-imidazol-1-ylmethyl)-1,3-dioxolan-4-yl]methoxy]-phenyl]-1-piperazinyl]phenyl]-2,4-dihydro-2-(2-oxocyclopentyl)-3H-1,2,4-triazol-3-one; (compound 103).

cis-4-[4-[4-[4-[[2-(2,4-difluorophenyl)-2-(1H-imidazol-1-ylmethyl)-1,3-dioxolan-4-yl]methoxy]-phenyl]-1- piperazinyl]phenyl]-2,4-dihydro-2-(2-oxocyclohexyl)-3H-1,2,4-triazol-3-one; (compound 104).

EXAMPLE 14

A mixture of 5.7 parts of 1-[4-[4-(4-hydroxyphenyl)-1-piperazinyl]phenyl]-3-(1-methyl-2-oxopropyl)-2-imidazolidinone, 6.8 parts of cis-2-(2,4-difluorophenyl)-2-(1H-1,2,4-triazol-1-ylmethyl)-1,3-dioxolane-4-methanol methanesulfonate(ester), 180 parts of N,N-dimethylformamide and 135 parts of benzene was stirred for a few minutes at 165° C. After the addition of 1.2 parts of sodium hydroxide, stirring was continued for 5 hours at room temperature and water was distilled off azeotropically. After cooling, the reaction mixture was diluted with water and the product was extracted twice with dichloromethane. The combined extracts were evaporated in vacuo and the residue was purified by column chromatography over silica gel using a mixture of trichloromethane and methanol (98.5:1.5 by volume) as eluent. The pure fractions were collected and the eluent was evaporated. The residue was triturated in methanol. The product was filtered off and crystallized from 4-methyl-2-pentanone, yielding 4.9 parts (50.8%) of cis-1-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-3-(1-methyl-2-oxopropyl)-2-imidazolidin-one; mp. 163.6° C. (compound 105).

In a similar manner there was also prepared:
cis-3-[4-[4-[4-[[2-(2,4-difluorophenyl)-2-(1H-imidazol-1-ylmethyl)-1,3-dioxolan-4-yl]methoxy]phenyl]-1-piperazinyl]phenyl]-5,5-dimethyl-1-(1-methyl-2-oxopropyl)-2,4-imidazolidinedione; mp. 115.5° C. (compound 106).

EXAMPLE 15

A mixture of 4.1 parts of 1-[4-[4-(4-hydroxyphenyl)-1-piperazinyl]phenyl]-3-(1-methyl-2-oxopropyl)-2-imidazolidinone, 5.0 parts of cis-2-(2,4-dichlorophenyl)-2-(1H-1,2,4-triazol-1-ylmethyl)-1,3-dioxolane-4-methanol methanesulfonate (ester), 3.0 parts of potassium carbonate, 135 parts of N,N-dimethylformamide and 90 parts of benzene was stirred overnight at 110° C. with azeotropic removal of water. After cooling, the reaction mixture was diluted with water and the product was extracted three times with dichloromethane. The combined extracts were washed twice with water and evaporated in vacuo. The residue was purified by column chromatography over silica gel using a mixture of trichloromethane and methanol (98.5:1.5 by volume) as eluent. The pure fractions were collected and the eluent was evaporated. The residue was triturated in methanol. The product was filtered off and crystallized from 4-methyl-2-pentanone. The product was filtered off and dried, yielding 3.3 parts (45.7%) of cis-1-[4-[-4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-3-(1-methyl-2-oxopropyl)-2-imidazolidinone; mp. 167.4° C. (compound 107).

In a similar manner there were also prepared:
cis-4-[4-[4-[4-[[2-(2-chloro-4-fluorophenyl)-2-(1H-imidazol-1-ylmethyl)-1,3-dioxolan-4-yl]methoxy]phenyl]-1-piperazinyl]phenyl]-2,4-dihydro-2-(1-methyl-2-oxopropyl)-3H-1,2,4-triazol-3-one: mp. 143.3° C. (compound 108).
cis-4-[4-[4-[4-[[2-(4-fluorophenyl)-2-(1H-imidazol-1-ylmethyl)-1,3-dioxolan-4-yl]methoxy]phenyl]-1-piperazinyl]phenyl]-2,4-dihydro-2-(1-methyl-2-oxopropyl)-3H-1,2,4-triazol-3-one; mp. 162.2° C. (compound 109).

EXAMPLE 16

A mixture of 2.4 parts of cis-3-[4-4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-5,5-dimethyl-1,2-[(tetrahydro-2H-pyran-2-yl)oxy]ethyl]-2,4-imidazolidinedione, 3.6 parts of concentrated hydrochloric acid, 40 parts of methanol and 50 parts of water was stirred overnight at room temperature. Water was added. The pH of the solution was adjusted to 9~10 with potassium carbonate. The product was crystallized, filtered off and taken up in dichloromethane. The organic layer was dried, filtered and evaporated in vacuo. The residue was triturated in methanol. The product was filtered off and crystallized from 4-methyl-2-pentanone, yielding 1.4 parts (60%) of cis-3-[4-[4-[4-[[2-(2,-dichlorophenyl)-2-(1H-1,2,4-triazol-1-ylmethyl)-1,3-dioxolan-4-yl]methoxy]phenyl]-1-piperazinyl]phenyl]-1-(2-hydroxyethyl)-5,5-dimethyl-2,4-imidazolidinedione; mp. 173.8° C. (compound 110).

In a similar manner there were also prepared:
cis-4-[4-[4-[4-[[2-(2,4-dichlorophenyl)-2-(1H-imidazol-1-ylmethyl)1,3-dioxolan-4-yl]methoxy]phenyl]-1-piperazinyl]phenyl]-2,4-dihydro-2-(3-hydroxypropyl)-3H-1,2,4-triazol-3-one; mp. 238.1° C. (compound 111);
cis-4-[4-[4-[4-[[2-(2,4-dichlorophenyl)-2-(1H-1,2,4-triazol-1-ylmethyl)-1,3-dioxolan-4-yl]1-piperazinyl]phenyl]-2-(2,3-dihydroxypropyl)-2,4-dihydro-5-methyl-3H-1,2,4-triazol-3-one; mp 174.8° C. (compound 112); and
cis-4-[4-[4-[4-[[2-(2,4-dichlorophenyl)-2-(1H-imidazol-1-ylmethyl)1,3-dioxolan-4-yl]methoxy]phenyl]-1-piperazinyl]phenyl]-2,4-dihydro-2-(2-hydroxyethyl)-5-methyl-3H-1,2,4-triazol-3-one; mp. 175.1° C. (compound 113).

EXAMPLE 17

A mixture of 3.5 parts of cis-4-[4-[4-[[2-(2,4-dichlorophenyl)-2-(1H-imidazol-1ylmethyl)1,3dioxolan-4]methoxy]phenyl]-1-piperazinyl]phenyl]-2-[(2,2-dimethyl-1,3-dioxolan-4-yl)-methyl]-2,4-dihydro-3H-1,2,4-triazol-3-one, 22.5 parts of tetrahydrofuran, 100 parts of water and 6 parts of concentrated hydrochloric acid was stirred overnight at room temperature. The reaction mixture was neutralized with potassium carbonate (9~10 pH). 150 parts of water were added. The product was filtered off, washed with water and crystallized from 1-butanol, yielding 1.8 parts (52%) of cis-4-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2-(2,3-dihydroxypropyl)- mp. 233.5° C. (compound 114).

In a similar manner there were also prepared:
cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(3-hydroxypropyl)-5-methyl-3H-1,2,4-triazol-3-one; mp. 103.3° C. (compound 115).
cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1-(3-hydroxypropyl)-5,5-dimethyl-2,4-imidazolidinedione; mp. 185.9° C. (compound 116).

EXAMPLE 18

A mixture of 2.8 parts of cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1-[(2,2-dimethyl-1,3-dioxolan-4-yl)methyl] 5,5-dimethyl-2,4-imidazolidinedione, 25 parts of 1.4-dioxane, 75 parts of water and 6 parts of concentrated hydrochloric acid was stirred overnight at room temperature. Water and potassium carbonate were added. The product was filtered off and crystallized from 4-methyl-2-pentanone. The product was filtered off and dried, yielding 1.6 parts (59%) of cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1-(2,3-dihydroxypropyl)-5,5-dimethyl-2,4-imidazolidinedione; mp. 170.8° C. (compound 117).

EXAMPLE 19

A mixture of 5.5 parts of cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methyl-2-oxo-2-phenylethyl)-3H-1,2,4-triazol-3-one, 2.0 parts of sodium tetrahydroborate and 120 parts of methanol was stirred overnight at room temperature. The reaction mixture was acidified with concentrated hydrochloric acid to pH 2 and the whole was stirred for 1 hour at room temperature. The reaction mixture was diluted with water and treated with potasssium carbonate to pH 9~10. The crystallized product was filtered off and dissolved in dichloromethane. The organic layer was dried (in the presence of activated charcoal), filtered and evaporated in vacuo. The residue was stirred in methanol. The product was filtered off and dried, yielding 4.2 parts (80%) of c is-4-[4-[4-[4-[[2-(2,4-difluorophenyl)-2-(1H-1,2,4-t riazol-1-ylmethyl)-1,3-dioxolan-4-yl]methoxy]phenyl]-1-piperazinyl]phenyl]-2,4-dihydro-2-(2-hydroxy-1-methyl-2-phenylethyl)-3H-1,2,4-triazol-3-one; mp. 192.5° C. (compound 118).

Following the same procedure and using equivalent amounts of the appropriate starting materials, there were also prepared:

cis-3-[4-[4-[4-[[2-(2,4-dichlorophenyl)-2-(1H-1,2,4-triazol-1-ylmethyl)-1,3-dioxolan-4-yl]methoxy]-phenyl]-1-piperazinyl]-phenyl]-1-(2-hydroxy-1-methylpropyl)-5,5-dimethyl-2,4-imidazolidinedione: mp. 135.6° C. (compound 119).

cis-4-[4-[4-[4-[[2-(2.4-dichlorophenyl)-2-(1H-imidazol-1-ylmethyl)-1,3-dioxolan-4-yl]methoxy]phenyl]-1-piperazinyl]phenyl]-2,4-dihydro-2 -(2-hydroxy-1-methylpropyl)-5-methyl-3H-1,2,4-triazol-3-one; mp. 124.2° C. (compound 120).

EXAMPLE 20

A mixture of 2.5 parts of cis-4-[4-[4-[2-(2,4-dichlorophenyl)-2-(1H-imidazol-1-ylmethyl)-1,3-dioxolan-4-yl]methoxy]phenyl]-1-piperazinyl]phenyl]-2,4-dihydro-2-(2-oxopropyl)-3H-1,2,4-triazol-3-one, 2.0 parts of sodium tetrahydroborate, 40 parts of methanol and 40 parts of acetonitrile was stirred overnight at room temperature. The pH of the solution was adjusted to 2 with concentrated hydrochloric acid and the reaction mixture was stirred for 30 minutes at room temperature. After the addition of 300 parts of water and potassium carbonate, the product was allowed to crystallize. The product was filtered off and crystallized from 2-propanol, yielding 2.1 parts (84%) of cis-4-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2,4-dihydro-2-(2-hydroxypropyl)-3H-1,2,4-triazol-3-one; mp. 207.4° C. (compound 121).

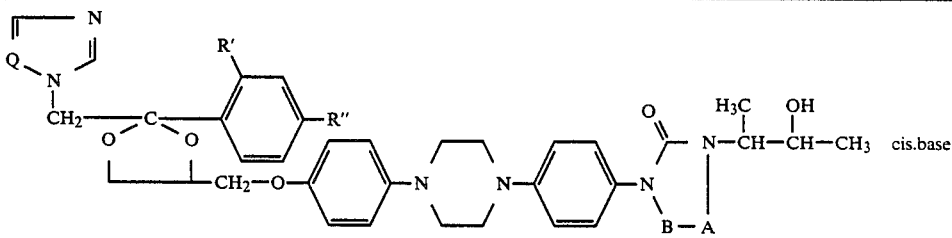

| No. | R' | R'' | Q | A—B | m.p. (°C.) |
| --- | --- | --- | --- | --- | --- |
| 122 | Cl | Cl | CH | N=CH | 196.0 |
| 123 | F | F | N | N=CH | 196.5 |
| 124 | Cl | Cl | CH | (CH$_3$)$_2$C—CO | 143.6 |
| 125 | Cl | Cl | N | CH$_2$—CH$_2$ | 145.2 |
| 126 | F | F | N | CH$_2$—CH$_2$ | 194.1 |
| 127 | Cl | F | CH | N=CH | 185.9 |
| 128 | H | F | CH | N=CH | 192.8 |
| 129 | H | F | N | CH$_2$—CH$_2$ | 163.5 |

EXAMPLE 21

To a stirred suspension of 2.7 parts of cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-phenyl]-2,4-dihydro-2-(1-methyl-2-oxopropyl)-3H-1,2,4-triazol-3-one, 80 parts of methanol and 10 parts of a sodium hydroxide solution 5N were added 0.160 parts of sodium tetrahydroborate. The whole was stirred first for 24 hours at room temperature and then for 24 hours in an oil bath at 40° C. 27 parts of tetrahydrofuran and 0.080 parts of sodium tetrahydroborate were added. After stirring for 24 hours in an oil bath at 40° C., the reaction mixture was evaporated in vacuo. The residue was stirred in water and acidified with acetic acid. After stirring for 15 minutes, the whole was treated with a potassium carbonate solution 10% and stirred for 45 minutes. The product was filtered off and crystallized from ethanol, yielding, after drying in vacuo for 20 hours at 90° C., 1.9 parts (70%) of cis-4-[4-[4-[4-[[2-(2,4--dichlorophenyl)-2-(1H-1,2,4-triazol-1-ylmethyl)-1,3- dioxolan-4-yl]methoxy]phenyl]-1-piperzainyl]-2,4-dihydro-2-(2-hydroxy-1-methylpropyl)-3H-1,2,4-triazol-3-one; mp

EXAMPLE 22

To a stirred mixture of 2.2 parts of 1,2-ethanedithiol, 3 parts of cis-4-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2-(2,2-diethoxyethyl)-2,4-dihydro-3H-1,2,4-triazol-3-one and 26 parts of dichloromethane were added 30 parts of methanesulfonic acid and the whole was stirred for 2 hours at room temperature. The reaction mixture was poured into a mixture of potassium carbonate and crushed ice. The product was extracted with dichloromethane. The extract was washed with a dilute sodium hydroxide solution, dried, filtered and evaporated. The residue was purified twice by column chromatography over silica gel using a mixture of trichloromethane and methanol (99.5:0.5 by volume) as eluent. The pure fractions were collected and the eluent was evaporated. The residue was triturated in ethyl acetate. The product was filtered off and crystallized from methylbenzene, yielding 1.05 parts of cis-4-[4-[4-[4-[[2-(2,4-dichlorophenyl)-2-(1H-imidazol-1-ylmethyl)-3-dioxolan-4-yl]methoxy]phenyl]-1-piperazinyl]phenyl]-2-[(1,3-dithiolan-2-yl)methyl]-2,4-dihydro-3H-1,2,4-triazol-3-one; mp. 186.8° C. (compound 131).

C. Pharmacological Examples

The strong anti-microbial activity of the compounds (I) is clearly evidenced by the data obtained in the following experiments, which data are only given to illustrate the useful anti-microbial properties of all the compounds (I) and not to limit the invention either with respect to the scope of susceptible microorganisms nor with respect to the scope of formula (I).

EXAMPLE 23

Oral and topical treatment of vaginal candidosis in rats

Female Wistar rats of ±100 g body weight were used. They were ovariectomized and hysterectomized and after three weeks of recovery, 100 μg of oestradiol undecylate in sesame oil was given subcutaneously once a week for 3 consecutive weeks. The thus induced pseudo-oestrus was controlled by microscopic examination of vaginal smears. Food and water were left available ad libitum. The rats were infected intravaginally with $8.10^5$ cells of *Candida albicans*, grown on Sabouraud broth for 48 hours at 37° C. and diluted with saline. The date of infection varies from day +25 to day +32 after surgical intervention, depending on the appearance of signs of induced pseudo-oestrus.

The drugs under investigation were administered orally once a day or topically twice a day for three consecutive days starting from the third day after infection. For each experiment there were placebo treated controls. The results were assessed by taking vaginal smears with sterile swabs on several days after the infection. The swabs were put into Sabouraud broth in petridishes and incubated for 48 hours at 37° C. If no growth of *Candida albicans* occurs, i.e., when the animals were negative at the end of the experiment, this was due to drug administration because it never happens in placebo-treated controls.

The first column in the Table I gives the lower oral dose in mg/kg of the drug under investigation which is found active at the 14th day after infection.

The second column in the Table I gives the lowest concentration of the drug under investigation which is found active at the 7th day after the last topical administration of the drug.

TABLE 1

| Compound No | Vaginal candidosis in rats Lowest oral dose in mg/kg | Vaginal candidosis in rats Lowest topical concentration (%) |
| --- | --- | --- |
| 23 | 1.25 | 0.125 |
| 24 | 1.25 | 0.031 |
| 25 | 0.63 | 0.063 |
| 28 | 0.63 | 0.063 |
| 29 | 0.63 | 0.031 |
| 32 | — | 0.031 |
| 6 | 1.25 | 0.063 |
| 35 | — | 0.031 |
| 37 | 0.63 | 0.125 |
| 36 | — | 0.031 |
| 60 | 1.25 | 0.031 |
| 130 | 1.25 | 0.031 |
| 89 | — | 0.063 |
| 68 | 1.25 | 0.25 |
| 71 | — | 0.063 |
| 78 | 0.63 | 0.031 |
| 79 | 0.63 | 0.125 |
| 123 | 1.25 | 0.016 |
| 105 | — | ≦0.031 |
| 125 | — | 0.063 |
| 126 | 1.25 | 0.031 |
| 77 | — | 0.125 |
| 106 | — | 0.063 |

D. Composition Examples

The following formulations exemplify typical pharmaceutical compositions in dosage unit form suitable for systemic administration to animal and human subjects in accordance with the instant invention.

"Active ingredient" (A.I.) as used throughout these examples relates to a compound of formula (I) or a pharmaceutically acceptable acid addition salt thereof.

EXAMPLE 24: ORAL DROPS 500 g of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg of the A.I. per ml. The resulting solution was filled into suitable containers.

EXAMPLE 25: ORAL SOLUTION 9 g of methyl 4-hydroxybenzoate and 1 g of propyl 4-hydroxy-benzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propane-triol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20

1 providing an oral solution comprising 20 mg of the active ingredient per teaspoonful (5 ml). The resulting solution was filled in suitable containers.

EXAMPLE 26: CAPSULES 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelating capsules, comprising each 20 mg of the active ingredient.

EXAMPLE 27: FILM-COATED TABLETS

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90®) in about 200 ml of water. The wet powder mixture was sieved, dried and sieved again. Then there was added 100 g microcrystalline cellulose (Avicel®) and 15 g hydrogenated vegetable oil (Sterotex®). The whole was mixed well and compressed into tablets, giving 10,000 tablets, each containing 10 mg of the active ingredient.

Coating

To a solution of 10 g methyl cellulose (Methocel 60 HG®) in 75 ml of denaturated ethanol there was added a solution of 5 g of ethyl cellulose (Ethocel 22 cps®) in 150 ml of dichloromethane. Then there were added 75 ml of dichloromethane and 2.5 ml 1,2,3-propane-triol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated colour suspension (Opaspray K-1-2109®) and the whole was homogenated. The tablet cores were coated with the thus obtained mixture in a coating apparatus.

EXAMPLE 28: INJECTABLE SOLUTION 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg A.I. per ml. The solution was sterilized by filtration (U.S.P. XVII p. 811) and filled in sterile containers.

EXAMPLE 29: SUPPOSITORIES 3 g A.I. was dissolved in a solution of 3 g 2,3-dihydroxybutanedoic acid in 25 ml polyethylene glycol 400. 12 g Surfactant (SPAN®) and triglycerides (Witepsol 555®) q.s. ad 300 g were molten together. The latter mixture was mixed well with the former solution. The thus obtained mixture was poured into moulds at a temperature of 37°~38° C. to form 100 suppositories each containing 30 mg of the active ingredient.

What we claim is:

1. A chemical compound having the formula

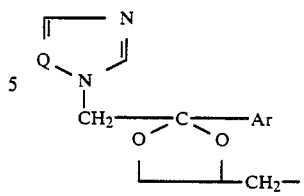
(I)

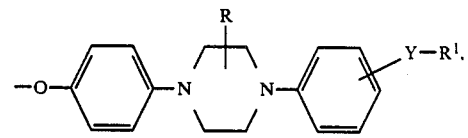

a pharmaceutically acceptable acid-addition salt or a stereochemically isomeric form thereof, wherein
Q is N or CH;
Ar is aryl;
R is hydrogen or $C_{1-6}$ alkyl; and
Y—$R^1$ is a radical having the formula

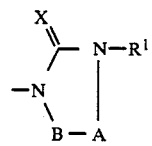
(a)

or a radical having the formula

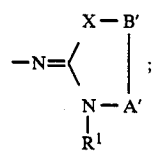
(b)

wherein
$R^1$ is tetrahydrofuranyl$C_{1-6}$ alkyl; or $C_{1-6}$ alkyl, $C_{3-6}$ cycloalkyl, aryl$C_{1-6}$ alkyl or ($C_{3-6}$ cycloalkyl)$C_{1-6}$ alkyl all substituted on the $C_{1-6}$ alkyl and/or $C_{3-6}$ cycloalkyl moiety with oxo, thioxo or with one or two radicals of formula —Z—$R^{1-a}$;
said Z being O or S;
said $R^{1-a}$ being hydrogen, $C_{1-6}$ alkyl, aryl, $C_{3-6}$ cycloalkyl or tetrahydro-2H-pyran-2-yl;
or where $R^1$ is substituted with two —Z—$R^{1-a}$ radicals, the two —$R^{1-a}$ radicals, taken together, may form a bivalent radical of formula —$CH_2$—, —$CH(CH_3)$—, —$C(CH_3)_2$—, —$CH_2$—$CH_2$—, —$CH(CH_3)$—$CH_2$— or —$CH_2$—$CH_2$—$CH_2$—;
X is O, S or $NR^2$;
said $R^2$ being hydrogen or $C_{1-6}$ alkyl;
A is >C=O, $NR^3$, methylene or methylene substituted with up to two radicals selected from the group consisting of $C_{1-6}$ alkyl and aryl;
said $R^3$ being hydrogen or $C_{1-6}$ alkyl;
B is >C=O or methylene optionally substituted with up to two $C_{1-6}$ alkyl radicals;
or A and B, taken together, form a bivalent radical of formula

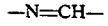
—N=CH— (c);

A' and B' independently having the same meaning of A and B respectively, or A' and B', taken together, form a bivalent radical of formula —N=CH— (c) or —CH=CH— (d);

wherein the nitrogen atom in the bivalent radical (c) is connected to $NR^1$; wherein one hydrogen in said radical (c) and up to two hydrogens in radical (d) may be replaced by a $C_{1-6}$ alkyl radical; provided that (i) when $Y-R^1$ is a radical of formula (a) wherein —A—B— is other than a bivalent radical of formula (c), then $R^1$ is other than $C_{1-6}$ alkyl substituted with $C_{1-6}$ alkyloxy;

(ii) when $Y-R^1$ is a radical of formula (b) then $R^1$ is other than $C_{1-6}$ alkyl substituted with $C_{1-6}$ alkyloxy;

wherein aryl is phenyl or substituted phenyl, said substituted phenyl having from 1 to 3 substituents each independently selected from the group consisting of fluoro, chloro, bromo, $C_{1-6}$ alkyl, $C_{1-6}$ alkyloxy, and trifluoromethyl.

2. A chemical compound according to claim 1 wherein $Y-R^1$ is a radical of formula (a) or (b), provided that A' and B', taken together, do not form a radical of formula (c) or (d).

3. A chemical compound according to claim 2 wherein $Y-R^1$ is a radical of formula (a).

4. A chemical compound according to claim 3 wherein X is O; A and B are independently >C=O or methylene optionally substituted with up to two $C_{1-6}$ alkyl radicals, or A and B, taken together, form a bivalent radical of formula (c) wherein the hydrogen atom may be replaced by a $C_{1-6}$ alkyl radical; and $R^1$ is tetrahydrofuranyl$C_{1-6}$ alkyl, or $C_{3-6}$cycloalkyl substituted with oxo or hydroxy, or $C_{1-6}$ alkyl or aryl$C_{1-6}$ alkyl both substituted on the $C_{1-6}$ alkyl moiety with oxo or with one or two radicals of formula —O—$R^{1-a}$, or where $R^1$ is substituted with two —O—$R^{1-a}$ radicals, the two —$R^{1-a}$ radicals, taken together, may form a bivalent radical of formula —C(CH$_3$)$_2$— or —CH$_2$—CH$_2$—.

5. A chemical compound according to claim 4 wherein $R^1$ is $C_{3-6}$ cycloalkyl substituted with oxo or hydroxy, or $C_{1-6}$ alkyl or aryl$C_{1-6}$ alkyl both substituted on the $C_{1-6}$ alkyl moiety with oxo or with one or two hydroxy or $C_{1-6}$ alkyloxy radicals.

6. A chemical compound according to claim 5 wherein Ar is phenyl substituted with two halo atoms; R is hydrogen; A is C(CH$_3$)$_2$ or CH$_2$, B is CH$_2$ or >C=O, or A and B, taken together, form a radical (c) wherein the hydrogen atom may be replaced by a methyl radical; and $R^1$ is $C_{1-6}$ alkyl substituted with oxo or hydroxy.

7. A composition for combatting microorganisms comprising an inert carrier material and as an active ingredient an antimicrobially effective amount of a compound having the formula

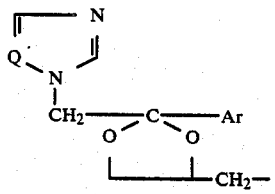

(I)

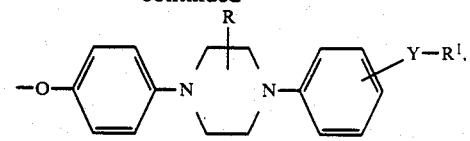

a pharmaceutically acceptable acid-addition salt or a stereochemically isomeric form thereof, wherein
Q is N or CH;
Ar is aryl;
R is hydrogen or $C_{1-6}$ alkyl; and
$Y-R^1$ is a radical having the formula

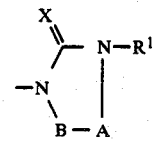

(a)

or a radical having the formula

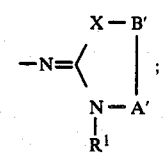

(b)

wherein
$R^1$ is tetrahydrofuranyl$C_{1-6}$ alkyl; or $C_{1-6}$ alkyl, $C_{3-6}$ cycloalkyl, aryl$C_{1-6}$ alkyl or ($C_{3-6}$ cycloalkyl)$C_{1-6}$ alkyl all substituted on the $C_{1-6}$ alkyl and/or $C_{3-6}$ cycloalkyl moiety with oxo, thioxo or with one or two radicals of formula —Z—$R^{1-a}$;
said Z being O or S;
said $R^{1-a}$ being hydrogen; $C_{1-6}$ alkyl, aryl, $C_{3-6}$ cycloalkyl or tetrahydro-2H-pyran-2-yl;
or where $R^1$ is substituted with two —Z—$R^{1-a}$ radicals, the two —$R^{1-a}$ radicals, taken together, may form a bivalent radical of formula —CH$_2$—, —CH(CH$_3$)—, —C(CH$_3$)$_2$—, —CH$_2$—CH$_2$—, —CH(CH$_3$)—CH$_2$— or —CH$_2$—CH$_2$—CH$_2$—;
X is O, S or NR$^2$;
said $R^2$ being hydrogen or $C_{1-6}$ alkyl;
A is >C=O, NR$^3$, methylene or methylene substituted with up to two radicals selected from the group consisting of $C_{1-6}$ alkyl and aryl;
said $R^3$ being hydrogen or $C_{1-6}$ alkyl;
B is >C=O or methylene optionally substituted with up to two $C_{1-6}$ alkyl radicals;
or A and B, taken together, form a bivalent radical of formula —N=CH— (c);

A' and B' independently having the same meaning of A and B respectively, or A' and B', taken together, form a bivalent radical of formula —N=CH— (c) or —CH=CH— (d);

wherein the nitrogen atom in the bivalent radical (c) is connected to $NR^1$; wherein one hydrogen in said radical (c) and up to two hydrogens in radical (d) may be replaced by a $C_{1-6}$ alkyl radical; provided that
  (i) when $Y-R^1$ is a radical of formula (a) wherein —A—B— is other than a bivalent radical of formula (c), then $R^1$ is other than $C_{1-6}$ alkyl substituted with $C_{1-6}$ alkyloxy;
  (ii) when $Y-R^1$ is a radical of formula (b) then $R^1$ is other than $C_{1-6}$ alkyl substituted with $C_{1-6}$ alkyloxy;
wherein aryl is phenyl or substituted phenyl, said substituted phenyl having from 1 to 3 substituents each independently selected from the group consisting of fluoro, chloro, bromo, $C_{1-6}$ alkyl, $C_{1-6}$ alkyloxy, and trifluoromethyl.

8. A composition according to claim 7 wherein $Y-R^1$ is a radical of formula (a) or (b), provided that A' and B', taken together, do not form a radical of formula (c) or (d).

9. A composition according to claim 8 wherein $Y-R^1$ is a radical of formula (a).

10. A composition according to claim 9 wherein X is O; A and B are independently >C=O or methylene optionally substituted with up to two $C_{1-6}$ alkyl radicals, or A and B, taken together, form a bivalent radical of formula (c) wherein the hydrogen atom may be replaced by a $C_{1-6}$ alkyl radical; and $R^1$ is tetrahydrofuranyl$C_{1-6}$ alkyl, or $C_{3-6}$ cycloalkyl substituted with oxo or hydroxy, or $C_{1-6}$ alkyl or aryl$C_{1-6}$ alkyl both substituted on the $C_{1-6}$ alkyl moiety with oxo or with one or two radicals of formula —O—$R^{1-a}$, or where $R^1$ is substituted with two —O—$R^{1-a}$ radicals, the two —$R^{1-a}$ radicals, taken together, may form a bivalent radical of formula —C(CH$_3$)$_2$— or —CH$_2$—CH$_2$—.

11. A composition according to claim 10 wherein $R^1$ is $C_{3-6}$ cycloalkyl substituted with oxo or hydroxy, or $C_{1-6}$ alkyl or aryl$C_{1-6}$ alkyl both substituted on the $C_{1-6}$ alkyl moiety with oxo or with one or two hydroxy or $C_{1-6}$ alkyloxy radicals.

12. A composition according to claim 11 wherein Ar is phenyl substituted with two halo atoms; R is hydrogen; A is C(CH$_3$)$_2$ or CH$_2$, B is CH$_2$ or >C=O, or A and B, taken together, form a radical (c) wherein the hydrogen atom may be replaced by a methyl radical; and $R^1$ is $C_{1-6}$ alkyl substituted with oxo or hydroxy.

13. A method of inhibiting and/or eliminating the development of fungi and bacteria in warm-blooded animals suffering from diseases caused by these fungi and/or bacteria by the systemic or topical a aministration of an antimicrobially effective amount of a compound having the formula

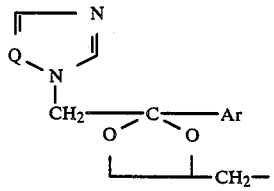
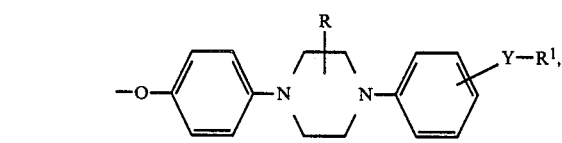

(I)

a pharmaceutically acceptable acid-addition salt or a stereochemically isomeric form thereof, wherein Q is N or CH;
Ar is aryl;
R is hydrogen or $C_{1-6}$ alkyl; and
$Y-R^1$ is a radical having the formula

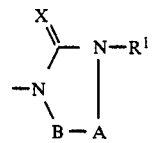

(a)

or a radical having the formula

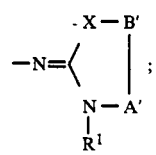

(b)

wherein
$R^1$ is tetrahydrofuranyl$C_{1-6}$ alkyl; or $C_{1-6}$ alkyl, $C_{3-6}$ cycloalkyl, aryl$C_{1-6}$ alkyl or ($C_{3-6}$ cycloalkyl)$C_{1-6}$ alkyl all substituted on the $C_{1-6}$ alkyl and/or $C_{3-6}$ cycloalkyl moiety with oxo, thioxo or with one or two radicals of formula —Z—$R^{1-a}$;
said Z being O or S;
said $R^{1-a}$ being hydrogen, $C_{1-6}$ alkyl, aryl, $C_{3-6}$ cycloalkyl or tetrahydro-2H-pyran-2-yl;
or where $R^1$ is substituted with two —Z—$R^{1-a}$ radicals, the two —$R^{1-a}$ radicals, taken together, may form a bivalent radical of formula —CH$_2$—, —CH(CH$_3$)—, —C(CH$_3$)$_2$—, —CH$_2$—CH$_2$—, —CH(CH$_3$)—CH$_2$— or —CH$_2$—CH$_2$—CH$_2$—;
X is O, S or NR$^2$;
said $R^2$ being hydrogen or $C_{1-6}$ alkyl;
A is >C=O, NR$^3$, methylene or methylene substituted with up to two radicals selected from the group consisting of $C_{1-6}$ alkyl and aryl;
said $R^3$ being hydrogen or $C_{1-6}$ alkyl;
B is >C=O or methylene optionally substituted with up to two $C_{1-6}$ alkyl radicals;
or A and B, taken together, form a bivalent radical of formula

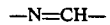 (c);

A' and B' independently having the same meaning of A and B respectively, or A' and B', taken together, form a bivalent radical of formula

 (c) or

 (d);

wherein the nitrogen atom in the bivalent radical (c) is connected to NR$^1$; wherein one hydrogen in said radical (c) and up to two hydrogens in radical (d) may be replaced by a $C_{1-6}$ alkyl radical; provided that
  (i) when $Y-R^1$ is a radical of formula (a) wherein —A—B— is other than a bivalent radical of formula (c), then $R^1$ is other than $C_{1-6}$ alkyl substituted with $C_{1-6}$ alkyloxy;
  (ii) when $Y-R^1$ is a radical of formula (b) then $R^1$ is other than $C_{1-6}$ alkyl substituted with $C_{1-6}$ alkyloxy;

wherein aryl is phenyl or substituted phenyl, said substituted phenyl having from 1 to 3 substituents each independently selected from the group consisting of fluoro, chloro, bromo, $C_{1-6}$ alkyl, $C_{1-6}$ alkyloxy, and trifluoromethyl.

14. A method according to claim 13 wherein Y—$R^1$ is a radical of formula (a) or (b), provided that A' and B', taken together, do not form a radical of formula (c) or (d).

15. A method according to claim 14 wherein Y—$R^1$ is a radical of formula (a).

16. A method according to claim 15 wherein X is O; A and B are independently >C=O or methylene optionally substituted with up to two $C_{1-6}$ alkyl radicals, or A and B, taken together, form a bivalent radical of formula (c) wherein the hydrogen atom may be replaced by a $C_{1-6}$ alkyl radical; and $R^1$ is tetrahydrofuranyl$C_{1-6}$ alkyl, or $C_{3-6}$ cycloalkyl substituted with oxo or hydroxy, or $C_{1-6}$ alkyl or aryl$C_{1-6}$ alkyl both substituted on the $C_{1-6}$ alkyl moiety with oxo or with one or two radicals of formula —O—$R^{1-a}$, or where $R^1$ is substituted with two —O—$R^{1-a}$ radicals, the two —$R^{1-a}$ radicals, taken together, may form a bivalent radical of formula —C(CH$_3$)$_2$— or —CH$_2$—CH$_2$—.

17. A method according to claim 16 wherein $R^1$ is $C_{3-6}$ cycloalkyl substituted with oxo or hydroxy, or $C_{1-6}$ alkyl or aryl$C_{1-6}$ alkyl both substituted on the $C_{1-6}$ alkyl moiety with oxo or with one or two hydroxy or $C_{1-6}$ alkyloxy radicals.

18. A method according to claim 17 wherein Ar is phenyl substituted with two halo atoms; R is hydrogen; A is C(CH$_3$)$_2$ or CH$_2$, B is CH$_2$ or >C=O, or A and B, taken together, form a radical (c) wherein the hydrogen atom may be replaced by a methyl radical; and $R^1$ is $C^{1-6}$ alkyl substituted with oxo or hydroxy.

19. A chemical compound according to claim 1, wherein A' and B' are both methylene or methylene substituted with up to two $C_{1-6}$alkyl radicals.

20. A substituted phenol of the following formula (V):

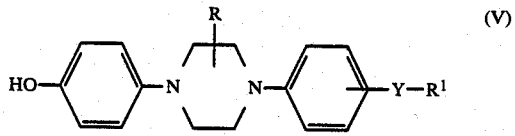

(V)

or a stereochemically isomeric form thereof, wherein R is hydrogen or $C_{1-6}$ alkyl; and Y—$R^1$ is a radical having the formula

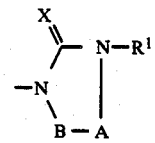

(a)

or a radical having the formula

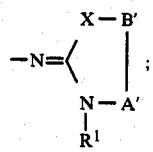

(b)

wherein
$R^1$ is tetrahydrofuranyl$C_{1-6}$ alkyl; or $C_{1-6}$ alkyl, $C_{3-6}$cycloalkyl, aryl$C_{1-6}$ alkyl or ($C_{3-6}$cycloalkyl)$C_{1-6}$ alkyl all substituted on the $C_{1-6}$ alkyl and/or $C_{3-6}$cycloalkyl moiety with oxo, thioxo or with one or two radicals of formula —Z—$R^{1-a}$;
said Z being O or S;
said $R^{1-a}$ being hydrogen, $C_{1-6}$ alkyl, aryl, $C_{3-6}$cycloalkyl or tetrahydro-2H-pyran-2-yl;
or wherein $R^1$ is substituted with two —Z—$R^{1-a}$ radicals, the two —$R^{1-a}$ radicals, taken together, may form a bivalent radical of formula —CH$_2$—, —CH(CH$_3$)—, —C(CH$_3$)$_2$—, —CH$_2$—CH$_2$—, —CH(CH$_3$)—CH$_2$— or —CH$_2$—CH$_2$—CH$_2$—;
X is O, S or NR$^2$;
said $R^2$ being hydrogen or $C_{1-6}$ alkyl;
A is >C=O, NR$^3$, methylene or methylene substituted with up to two radicals selected from the group consisting of $C_{1-6}$ alkyl and aryl;
said $R^3$ being hydrogen or $C_{1-6}$ alkyl;
B is >C=O or methylene optionally substituted with up to two $C_{1-6}$ alkyl radicals;
or A and B, taken together, form a bivalent radical of formula

         (c);

A' and B' independently having the same meaning of A and B respectively, or A' and B', taken together, form a bivalent radical of formula

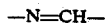         (c) or

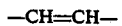         (d);

wherein the nitrogen atom in the bivalent radical (c) is connected to NR$^1$; wherein one hydrogen in said radical (c) and up to two hydrogens in radical (d) may be replaced by a $C_{1-6}$ alkyl radical; provided that
(i) when Y—$R^1$ is a radical of formula (a) wherein —A—B— is other than a bivalent radical of formula (c), then $R^1$ is other than $C_{1-6}$ alkyl substituted with $C_{1-6}$ alkyloxy;
(ii) when Y—$R^1$ is a radical of formula (b) then $R^1$ is other than $C_{1-6}$ alkyl substituted with $C_{1-6}$ alkyloxy;
wherein aryl is phenyl or substituted phenyl, said substituted phenyl having from 1 to 3 substituents each independently selected from the group consisting of fluoro, chloro, bromo, $C_{1-6}$ alkyl, $C_{1-6}$ alkyloxy and trifluoromethyl.

21. A chemical compound according to claim 20, wherein Y—$R^1$ is a radical of formula (a) or (b), provided that A' and B', taken together, do not form a radical of formula (c) or (d).

22. A chemical compound according to claim 21, wherein Y—$R^1$ is a radical of formula (a).

23. A chemical compound according to claim 21, wherein X is O; A and B are independently >C=O, methylene or methylene optionally substituted with up to two $C_{1-6}$ alkyl radicals, or A and B, taken together, form a bivalent radical of formula (c) wherein the hydrogen atom may be replaced by a $C_{1-6}$ alkyl radical; and $R^1$ is tetrahydrofuranyl$C_{1-6}$ alkyl, or $C_{3-6}$cycloalkyl substituted with oxo or hydroxy, or $C_{1-6}$ alkyl or aryl$C_{1-6}$ alkyl both substituted on the $C_{1-6}$ alkyl moiety with oxo or with one or two radicals of formula —O—R$^{1-a}$, or where R$^1$ is substituted with two —O—R$^{1-a}$ radicals, the two —R$^{1-a}$ radicals, taken together, may form a bivalent radical of formula —C(CH$_3$)$_2$— or —CH$_2$—CH$_2$—.

24. A chemical compound according to claim 23, wherein R$^1$ is C$_{3-6}$cycloalkyl substituted with oxo or hydroxy, or C$_{1-6}$ alkyl or arylC$_{1-6}$ alkyl both substituted on the C$_{1-6}$ alkyl moiety with oxo or with one or two hydroxy or C$_{1-6}$ alkyloxy radicals.

25. A compound according to claim 20, wherein the compound is:
2-[2-(4-bromophenyl)-1-methyl-2-oxoethyl]-2,4-dihydro-4-[4-[4-(4-hydroxyphenyl)-1-piperazinyl]phenyl]-3H-1,2,4-triazol-3-one;
2,4-dihydro-4-[4-[4-(4-hydroxyphenyl)-1-piperazinyl]phenyl]-2-(2-oxocyclopentyl)-3H-1,2,4-triazol-3-one;
2,4-dihydro-4-[4-[4-(4-hydroxyphenyl)-1-piperazinyl]phenyl]-2-(2-oxocyclohexyl)-3H-1,2,4-triazol-3-one.

* * * * *